United States Patent
Pallett et al.

(10) Patent No.: US 8,642,509 B2
(45) Date of Patent: Feb. 4, 2014

(54) HERBICIDAL COMPOSITIONS

(75) Inventors: Ken Pallett, Königstein (DE); Ashley Slater, Essex (GB)

(73) Assignee: Aventis Cropscience UK Limited, Hauxton, Cambridge (GB)

( * ) Notice: Subject to any disclaimer, the term of this patent is extended or adjusted under 35 U.S.C. 154(b) by 281 days.

(21) Appl. No.: 11/475,812

(22) Filed: Jun. 27, 2006

(65) Prior Publication Data

US 2006/0240984 A1 Oct. 26, 2006

Related U.S. Application Data

(63) Continuation of application No. 10/049,731, filed as application No. PCT/CT00/09339 on Sep. 8, 2000, now abandoned.

(30) Foreign Application Priority Data

Sep. 8, 1999 (GB) .................................. 9921220.1
May 19, 2000 (GB) .................................. 0012090.7

(51) Int. Cl.
*A01N 43/72* (2006.01)

(52) U.S. Cl.
USPC .......................................................... 504/223

(58) Field of Classification Search
None
See application file for complete search history.

(56) References Cited

U.S. PATENT DOCUMENTS

| | | | | |
|---|---|---|---|---|
| 5,334,753 | A | 8/1994 | Bennetau et al. | 562/405 |
| 5,441,922 | A | 8/1995 | Ort et al. | |
| 5,516,750 | A * | 5/1996 | Willms et al. | 504/106 |
| 5,561,100 | A | 10/1996 | Hagen et al. | 504/130 |
| 5,627,131 | A * | 5/1997 | Shribbs et al. | 504/105 |
| 5,631,210 | A * | 5/1997 | Tseng | 504/282 |
| 5,650,533 | A | 7/1997 | Roberts et al. | 560/17 |
| 5,656,573 | A * | 8/1997 | Roberts et al. | 504/271 |
| 5,747,424 | A | 5/1998 | Roberts et al. | 504/271 |
| 5,804,432 | A | 9/1998 | Knapp | |
| 5,804,532 | A * | 9/1998 | Cain et al. | 504/309 |
| 5,837,652 | A * | 11/1998 | Anderson-Taylor et al. | 504/138 |
| 5,859,283 | A | 1/1999 | Cramp | 560/124 |
| 5,863,865 | A * | 1/1999 | Lee et al. | 504/271 |
| 5,905,057 | A * | 5/1999 | Forget et al. | 504/271 |
| 6,013,805 | A * | 1/2000 | Hawkins | 548/248 |
| 6,214,770 | B1 * | 4/2001 | Millet et al. | 504/138 |
| 6,297,198 | B1 * | 10/2001 | Lee | 504/271 |
| 6,489,267 | B1 | 12/2002 | Ruegg et al. | |
| 6,746,987 | B2 | 6/2004 | Rüegg | |
| 7,141,531 | B2 * | 11/2006 | Willms et al. | 504/106 |
| 2001/0044382 | A1 * | 11/2001 | Ruegg | 504/139 |
| 2006/0030485 | A1 | 2/2006 | Ziemer et al. | |

FOREIGN PATENT DOCUMENTS

| | | |
|---|---|---|
| CA | 2334955 | 6/1999 |
| DE | 43 16 880 A1 | 11/1993 |
| DE | 4316880 | 11/1993 |
| DE | 43 31 448 A1 | 3/1995 |
| DE | 4440354 * | 5/1996 |
| DE | 19711953 * | 9/1997 |
| DE | 19853827 | 5/2000 |
| EP | 0 298 680 A2 | 1/1989 |
| EP | 0298680 | 1/1989 |
| EP | 487357 * | 11/1991 |
| EP | 0 496 631 A1 | 7/1992 |
| EP | 496631 * | 7/1992 |
| EP | 0 551 650 A2 | 7/1993 |
| EP | 0551650 | 7/1993 |
| EP | 918 056 * | 5/1999 |
| HU | P9300293 (217562) | 5/1993 |
| HU | P9202531 (212433) | 6/1996 |
| HU | P9301669 (213371) | 5/1997 |
| HU | P9202532 (218304) | 7/2000 |
| WO | WO 95/07897 | 3/1995 |
| WO | WO 96/14747 | 5/1996 |
| WO | WO 96/21357 | 7/1996 |
| WO | 97/34485 | 9/1997 |
| WO | WO 97/34485 | 9/1997 |
| WO | 98/13361 | 4/1998 |
| WO | WO 98/13361 | 4/1998 |
| WO | WO 98/56251 | 12/1998 |
| WO | WO-9909023 * | 2/1999 |
| WO | 99/66795 | 12/1999 |
| WO | WO 99/65314 | 12/1999 |
| WO | WO 99/66795 | 12/1999 |
| WO | 00/00029 | 1/2000 |
| WO | 00/00031 | 1/2000 |
| WO | WO 00/00029 | 1/2000 |
| WO | WO 00/00031 | 1/2000 |

(Continued)

OTHER PUBLICATIONS

Sprague et al., "Enhancing the Margin of Selectivity of RPA 201772 in *Zea mays* with Antidotes," Weed Science, vol. 47, (1999), pp. 492-497
Menendez et al., "Meded—Fac. Landbouwkd. Toegepaste Biol. Wet. (Univ. Gent)", vol. 63(3a), (1998), pp. 761-767.
Pallett et al., "Extended Summary: New Perspectives in Mechanisms of Herbicide Action," Pestic. Sci., vol. 50, (1997), pp. 83-84.
Böger, P., "Mode of Action of Herbicides Affecting Carotenogenesis," J. Pesticide Sci., vol. 21, (1996), pp. 473-478.
Pallett, et al., "Extended Summary: New Perspectives in Mechanisms of Herbicide Action," Pestic. Sci., vol. 50 (1997), pp. 83-84.
Böger, P., "Mode of Action of Herbicides Affecting Carotenogenesis," J. Pesticide Sci., vol. 21 (1996), pp. 473-478.

(Continued)

*Primary Examiner* — Alton Pryor

(74) *Attorney, Agent, or Firm* — Frommer Lawrence & Haug LLP

(57) ABSTRACT

The present invention provides a method of reducing phytotoxicity to crops (especially maize) caused by a herbicidal benzoylisoxazole and/or dione derivative of formula (I) or an agriculturally acceptable salt or metal complex thereof; which method comprises applying to the locus of the crop an antidotally effective amount of an antidote compound, optionally with a partner herbicide.

38 Claims, No Drawings

(56) References Cited

FOREIGN PATENT DOCUMENTS

| WO | WO0000031 | * | 1/2000 |
| WO | WO 00/08923 | | 2/2000 |
| WO | 00/30447 | | 6/2000 |
| WO | WO 00/30447 | | 6/2000 |
| WO | WO0074488 | * | 12/2000 |
| WO | WO 01/17350 A1 | | 3/2001 |

OTHER PUBLICATIONS

Sprague, et al., "Enhancing the Margin of Selectivity of RPA 201772 in *Zea mays* with Antidotes," Weed Science, vol. 47, (1999), pp. 492-497.

Sprague et al; Enhancing the Margin of Selectivity of RPA 201772 in *Zea mays* with Antidotes, Weed Science, 47, pp. 492-497, 1999.

Menendez et al., "Meded—Fac. Landbouwkd. Toegepaste Biol. Wet. (Univ. Gent)", vol. 63(3a), pp. 761-767 (1998).

* cited by examiner

HERBICIDAL COMPOSITIONS

The application is a continuation of Ser. No. 10/049,731 filed Feb. 15, 2002 now abandon which is a 371 of PCT/EP00/09339 filed Sep. 8, 2000.

BACKGROUND OF THE INVENTION

The present invention relates to the safening of herbicidal compounds, in particular the safening of benzoylisoxazole and/or dione derivatives which are useful for the growing of crops in particular for maize (*Zea mays*) and to compositions useful for such treatment.

DISCUSSION OF RELATED ART

An important factor influencing the usefulness of a given herbicide is its selectivity toward crops. In some cases, a beneficial crop is susceptible to the effects of a herbicide when applied at application rates needed to control weed growth. In addition, certain herbicidal compounds are phytotoxic to some weed species but not to others. This may render such herbicides unsuitable for controlling weeds in the presence of certain crops. To be effective, a herbicide must cause minimal damage (preferably no damage) to the beneficial crop while maximising the damage to weed species which infest the locus of the crop. Reduction in herbicidal injury to crops without an unacceptable reduction in the herbicidal action can be accomplished by the use of crop protectants known as "antidotes" or "safeners". Identification of an antidote which safens a herbicide in crops is a complicated task. The precise mechanism by which an antidote reduces herbicidal crop injury has not been established. In general, the safening effect of a compound is specific to the herbicidal partner and the crop where the active ingredients are applied. Benzoylisoxazoles are known to possess herbicidal properties for example, European Patent Publication Nos. 0418175, 0487357, 0527036 and 0560482. European Patent Publication Nos. 0496630, 0496631, 0625505 and 0625508 disclose certain dione derivatives possessing herbicidal properties. In general such herbicides are very active against broad-leafed and grass weeds by pre- and/or post-emergence application. The method of controlling vegetation with these compounds comprises applying a herbicidally effective amount of the compounds, usually with an inert carrier or diluent, to the area where herbicidal control is desired. However, the herbicidal benzoylisoxazole and/or dione compounds have been found in some instances to adversely affect or interfere with the development of crop plants, especially maize crops. The effective use of these herbicides for controlling weeds in the presence of such crops may be enhanced by, or may require in certain instances, the addition of a compound which is antidotally effective with the herbicide.

Although it is possible to say in general terms that herbicides may be used in the presence of an antidote, the problem in identifying specific antidotes for specific crops at appropriate rates to control weed growth, is substantial.

The applicants have found that certain compounds, in particular when applied as described hereinafter, are effective antidotes for the protection of crops, especially maize crops, from herbicidal injury or the reduction of herbicidal injury caused by the application of an amount of a benzoylisoxazole and/or dione compound (optionally in admixture with a partner herbicide) effective to control the growth of weeds.

It is an object of the present invention to provide compositions of benzoylisoxazoles and/or dione herbicides in combination with antidotes, said compositions providing a reduction in crop injury, especially to maize (*Zea mays*), arising from the phytotoxicity of the herbicides, and a method of using said herbicides and antidotes.

DESCRIPTION OF THE INVENTION

The present invention provides a method of reducing phytotoxicity to a crop (especially maize) at a locus caused by the application thereto of a herbicidal benzoylisoxazole and/or dione derivative of formula (I):

(I)

wherein:

A is a group (A-1) to (A-7):

(A-1)

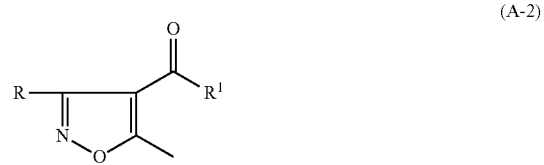

(A-2)

(A-3)

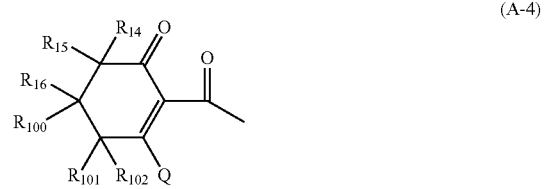

(A-4)

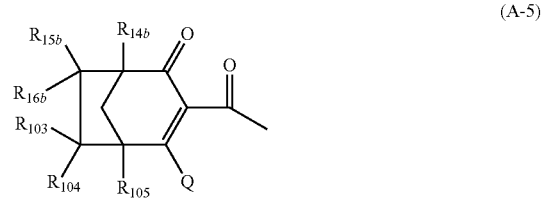

(A-5)

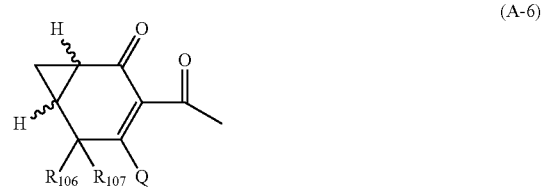

(A-6)

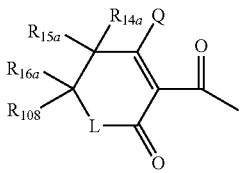
(A-7)

or a corresponding formula (A-6a) or (A-7a):

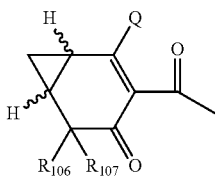
(A-6a)

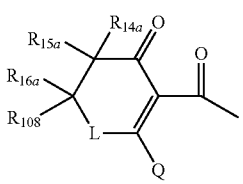
(A-7a)

in which the position of the carbonyl group and the group Q are reversed and the double bond in the ring is attached to the carbon atom attached to the group Q;

R is a hydrogen atom or a halogen atom; a straight- or branched chain alkyl, alkenyl or alkynyl group containing from one to six carbon atoms which is optionally substituted by one or more halogen atoms; a cycloalkyl group containing from 3 to 6 carbon atoms optionally substituted by one or more groups $R^5$, one or more halogen atoms or a group $—CO_2R^3$; or a group selected from $—CO_2R^3$, $—COR^5$, cyano, nitro, $—CONR^3R^4$ and $—S(O)_kR^{13}$;

$R^1$ is a straight- or branched-chain alkyl, alkenyl or alkynyl group containing up to six carbon atoms which is optionally substituted by one or more halogen atoms; or a cycloalkyl group containing from three to six carbon atoms optionally substituted by one or more groups $R^5$ or one or more halogen atoms;

$R^2$ is a halogen atom; a straight- or branched-chain alkyl, alkenyl or alkynyl group containing up to six carbon atoms which is optionally substituted by one or more halogen atoms; a straight- or branched-chain alkyl group containing up to six carbon atoms which is substituted by one or more groups $—OR^5$; or a group selected from nitro, cyano, $—CO_2R^5$, $—S(O)_qR^6$, $—O(CH_2)_mOR^5$, $—COR^5$, $—NR^{11}R^{12}$, $—N(R^8)SO_2R^7$, $—N(R^8)CO_2R^7$, $—OR^5$, $—OSO_2R^7$, $—SO_2NR^3R^4$, $—CONR^3R^4$, $—CSNR^3R^4$, $—(CR^9R^{10})_y—S(O)_qR^7$ and $—SF_5$;

or two groups $R^2$, on adjacent carbon atoms of the phenyl ring may, together with the carbon atoms to which they are attached, form a 5 to 7 membered saturated or unsaturated heterocyclic ring containing up to three ring heteroatoms selected from nitrogen, oxygen and sulfur, which ring is optionally substituted by one or more groups selected from halogen, nitro, $—S(O)_pR^{13}$, $C_{1-4}$ alkyl, $C_{1-4}$ alkoxy, $C_{1-4}$ haloalkyl, $C_{1-4}$ haloalkoxy, $=O$ (or a 5- or 6-membered cyclic acetal thereof), and $=NO—R^3$, it being understood that a sulphur atom, where present in the ring, may be in the form of a group $—SO—$ or $—SO_2—$;

z is an integer from one to five: when z is greater than one the groups $R^2$ may be the same or different;

$R^3$, $R^4$ and $R^{109}$ are each independently a hydrogen atom, or a straight- or branched chain alkyl group containing up to six carbon atoms which is optionally substituted by one or more halogen atoms;

$R^5$ and $R^{110}$ are each independently a straight- or branched-chain alkyl group containing up to six carbon atoms which is optionally substituted by one or more halogen atoms or a straight- or branched-chain alkenyl or alkynyl group containing from two to six (preferably from three to six) carbon atoms which is optionally substituted by one or more halogen atoms;

$R^6$ and $R^7$, which may be the same or different, are each $R^5$; or phenyl optionally substituted by from one to five groups which may be the same or different selected from a halogen atom, a straight- or branched-chain alkyl group containing up to six carbon atoms which is optionally substituted by one or more halogen atoms, nitro, cyano, $—CO_2R^5$, $—S(O)_pR^{13}$, $—NR^{11}NR^{12}$, $—OR^5$ and $—CONR^3R^4$;

$R^8$, $R^9$ and $R^{10}$ are each a hydrogen atom or $R^6$;

$R^{11}$ and $R^{12}$ are each a hydrogen atom or $R^5$;

$R^{13}$ and $R^{111}$ are each a straight- or branched-chain alkyl group containing up to six carbon atoms which is optionally substituted by one or more halogen atoms;

Q is hydroxy, C1-6 alkoxy, $OR^{112}$, $SR^{112}$ or $SR^{111}$;

L is oxygen or $NR^{109}$;

$R^{14}$, $R^{14a}$, $R^{14b}$, $R^{15}$, $R^{15a}$, $R^{15b}$, $R^{16}$, $R^{16a}$, $R^{16b}$, $R^{100}$, $R^{101}$, $R^{102}$, $R^{103}$, $R^{104}$, $R^{105}$, $R^{106}$, $R^{107}$ and $R^{108}$ are each the same or different groups selected from hydrogen, $R^{110}$, $—(CH_2)_uCO_2R^{109}$, halogen, cyano, C1-6 alkoxy, $—(CH_2)_x$-[phenyl optionally substituted by from one to five groups $R^{113}$ which may be the same or different], and cycloalkyl containing from three to six carbon atoms optionally substituted by C1-6 alkyl or $—S(O)_pR^{111}$;

$R^{112}$ is phenyl optionally substituted by from one to five groups selected from halogen, C1-6 alkyl, C1-6 haloalkyl, C1-6 alkoxy and nitro;

$R^{113}$ is a group selected from halogen, $R^{114}$, nitro, cyano, $—CO_2R^{115}$, $—S(O)_pR^{111}$, $—OR^{111}$ and $—NR^{115}R^{116}$;

$R^{114}$ is a straight- or branched-chain alkyl group containing one to three carbon atoms optionally substituted by one or more halogen atoms;

$R^{115}$ and $R^{116}$ which may be the same or different, are each a hydrogen atom or $R^{110}$;

p, q and u are each independently zero, one or two;

k and m are each one, two or three;

x is zero or one;

y is an integer from one to four; when y is greater than one, the groups $R^9$ and $R^{10}$ may be the same or different;

or an agriculturally acceptable salt or metal complex thereof; which method comprises applying to the locus of the crop, preferably before the herbicidal compound, an antidotally effective amount of an antidote compound, and optional partner herbicide.

It will be understood that the said antidote is, in general, antidotally effective for said benzoylisoxazole and/or dione derivative.

It will be understood that antidotes used in the method of the invention may form for example salts, and that the use of such salts is also embraced by the invention.

In this patent specification including the accompanying claims it is understood that the term 'agriculturally acceptable salts' is meant salts the cations or anions of which are known and accepted in the art for the formation of salts for agricultural or horticultural use. Preferably the salts are water-soluble. Suitable salts with bases include alkali metal (e.g. sodium and potassium), alkaline earth metal (e.g. calcium and magnesium), ammonium and amine (e.g. diethanolamine, triethanolamine, octylamine, morpholine and dioctylmethylamine) salts. Suitable acid addition salts, e.g. formed by compounds of formula (I) containing an amino group, include salts with inorganic acids, for example hydrochlorides, sulphates, phosphates and nitrates and salts with organic acids for example acetic acid.

It will be understood that the term 'dione' as used in this specification including the accompanying claims does not exclude the possible presence of additional C=O groups as in triones.

By the term "metal complexes" is meant compounds in which one or both of the oxygen atoms of the 1,3-dione of formula (A-3), (A-4), (A-5), (A-6), (A-7), (A-6a) or (A-7a) act as chelating agents to a metal cation. Examples of such cations include zinc, manganese, cupric, cuprous, ferric, ferrous, titanium and aluminium.

Compounds of formula (I) may exist in enolic tautomeric forms that may give rise to geometric isomers around the enolic double bond. Furthermore in certain cases the above substituents may contribute to optical isomerism and/or stereoisomerism. All such forms and mixtures thereof are embraced by the present invention.

It is to be understood that in this specification compounds comprising a cyclohexane ring corresponding to formula (A-6) or (A-7) or a precursor thereof include the compounds with the corresponding formula (A-6a) or (A-7a) or precursors thereof.

In the definitions of symbols in this specification including the accompanying claims unless otherwise specified the following definitions generally apply to the radicals in the formulae (I), (Ia) and (Ib) below:—

'halogen' means a fluorine, chlorine, bromine or iodine atom; and alkyl groups and moieties are straight or branched chain and contain from 1 to 6 carbon atoms.

Preferably A is a group of formula (A-1), (A-2), (A-3) or (A-4) (compounds of formula (A-1) are most preferred).

The benzoyl ring of the compounds of formula (I) is preferably 2,4-disubstituted, 2,3-disubstituted or 2,3,4-trisubstituted.

Preferably in formulae (A-4) to (A-7), the groups $R^{14}$, $R^{15}$, $R^{16}$, $R^{100}$, $R^{101}$, $R^{102}$, $R^{14a}$, $R^{15a}$, $R^{16a}$, $R^{103}$, $R^{14b}$, $R^{15b}$, $R^{16b}$, $R^{104}$, $R^{105}$ and $R^{108}$ are each hydrogen or lower alkyl (preferably hydrogen, methyl or ethyl); L (in A-7a) is NH; and Q is hydroxy or —S-phenyl.

Compounds of formula (I) in which A is (A-1), (A-2) or (A-3); R is hydrogen or —$CO_2R^3$ (in A-1 or A-2) wherein $R^3$ is a straight- or branched chain alkyl group containing up to three carbon atoms; and $R^1$ is cyclopropyl are preferred.

A further preferred class of compounds of formula (I) wherein A is (A-1) are those wherein:
R is hydrogen or —$CO_2Et$;
$R^1$ is cyclopropyl;
and two groups $R^2$, on adjacent carbon atoms of the phenyl ring may, together with the carbon atoms to which they are attached, combine to form a 5 or 6 membered saturated or unsaturated heterocyclic ring which is fused to the 2,3 or 3,4 positions of the benzoyl ring; wherein the heterocyclic ring contains two hetero atoms selected from sulphur and oxygen which are attached to the 2 and 3, or 3 and 4 positions of the benzoyl ring; and in which the 4-substituent of the benzoyl ring is halogen or $S(O)_pMe$, or the 2-substituent of the benzoyl ring is methyl, $S(O)_pMe$ or —$CH_2S(O)_qMe$ respectively; and optionally the heterocyclic ring may be substituted by one or more halogen atoms.

A further preferred class of compounds of formula (I) are those wherein A is (A-1); R is hydrogen or —$CO_2Et$; $R^1$ is cyclopropyl; $R^2$ is a halogen atom or a group selected from —$CF_3$, Me, Et, —$S(O)_pMe$, —$CH_2S(O)_qMe$ and optionally halogenated methoxy or ethoxy; and z is two or three.

A further preferred class of compounds of formula (I) wherein A is (A-4) are those wherein:
$R^{14}$, $R^{15}$, $R^{16}$, $R^{100}$, $R^{101}$ and $R^{102}$ are each hydrogen;
and two groups $R^2$, on adjacent carbon atoms of the phenyl ring may, together with the carbon atoms to which they are attached, combine to form a 6 membered saturated heterocyclic ring which is fused to the 2,3 or 3,4 positions of the benzoyl ring; wherein the heterocyclic ring contains a sulphur atom attached to the 4 position of the benzoyl ring, optionally in the form of a group —SO— or —$SO_2$—, and which ring is substituted by a 5- or 6-membered acetal thereof.

A more preferred class of compounds of formula (I) having the formula (Ia):

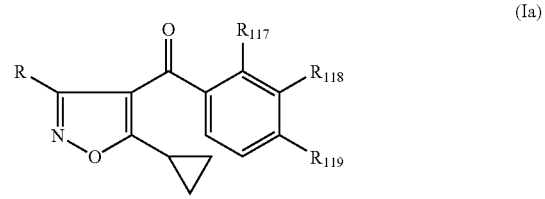

(Ia)

are those wherein:

R is hydrogen or —$CO_2Et$;

$R^{117}$ is selected from —$S(O)_pMe$, Me, Et, a chlorine, bromine or fluorine atom, methoxy, ethoxy and —$CH_2S(O)_qMe$;

$R^{118}$ is selected from a hydrogen atom, a chlorine, bromine or fluorine atom, methoxy, ethoxy and —$S(O)_pMe$;

$R^{119}$ is selected from a hydrogen atom, a chlorine, bromine or fluorine atom, methoxy and $CF_3$; and p and q each independently have the values zero, one or two.

An especially preferred class of compounds of formula (I) have the formula (Ib):

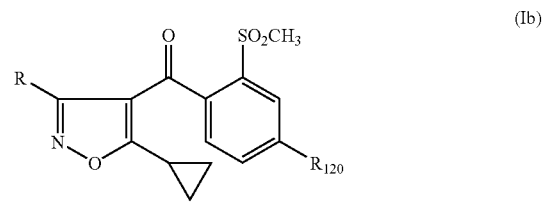

(Ib)

wherein $R^{120}$ is chlorine, bromine or trifluoromethyl; and

R is hydrogen or —$CO_2Et$.

Preferred diones are those in which a substituted phenyl ring as defined in formula (I); (Ia); or (Ib), is attached to a grouping;

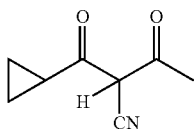

Such diones in which the phenyl ring is substituted by two groups independently selected from halogen, alkyl, S(O)$_p$alkyl (p=0, 1 or 2) and haloalkyl are also preferred.

Preferred triones are those in which a substituted phenyl ring, as defined above, is attached to a grouping;

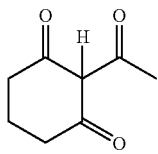

The following compounds of formula (I) are among the most preferred for use in the present invention:

5-cyclopropyl-4-[2-chloro-3-ethoxy-4-(ethylsulphonyl)benzoyl]isoxazole;
4-(4-chloro-2-methylsulphonylbenzoyl)-5-cyclopropylisoxazole;
5-cyclopropyl-4-(2-methylsulphonyl-4-trifluoromethylbenzoyl)isoxazole;
4-(4-bromo-2-methylsulphonylbenzoyl)-5-cyclopropylisoxazole;
5-cyclopropyl-4-[4-fluoro-3-methoxy-2-(methylsulphonyl)benzoyl]isoxazole;
4-(4-bromo-2-methylsulphonylmethylbenzoyl)-5-cyclopropylisoxazole;
ethyl 5-cyclopropyl-4-(2-methylsulphonyl-4-trifluoromethylbenzoyl)isoxazole-3-carboxylate;
2-[2-chloro-(4-methylsulphonyl)benzoyl]-1,3-cyclohexanedione;
2-[2-nitro-(4-methylsulphonyl)benzoyl]-1,3-cyclohexanedione;
2-(2,3-dihydro-5,8-dimethyl-1,1-dioxospiro[4H-1-benzothiin-4,2'-[1,3]dioxolan]-6-ylcarbonyl)cyclohexane-1,3-dione;
5-cyclopropyl-4-(2-methylsulphonyl-4-trifluoromethylbenzoyl)-3-methylthio-isoxazole; and
2-cyano-3-cyclopropyl-1-(2-methylsulphonyl-4-trifluoromethylphenyl)propan-1,3-dione.

The most preferred compounds are 5-cyclopropyl-4-(2-methylsulphonyl-4-trifluoromethylbenzoyl)isoxazole and 2[-2-nitro-(4-methylsulphonyl)benzoyl]-1,3-cyclohexanedione.

Herbicidal benzoylisoxazole and/or dione compounds for use in this invention may be prepared by the methods described in the aforementioned patent publications, or by the application or adaptation of known methods used or described in the chemical literature.

It has been found that the aforementioned antidote compounds can be selected from a wide range of chemical substances. The preferred compositions of this invention may include one or more antidotes which are not suggested by earlier antidotes which have been proposed for use with the benzoylisoxazole and/or dione derivatives of formula (I). The compositions of the invention may include one or more of the following antidotes:

a) compounds of the formulae (II) and (III),

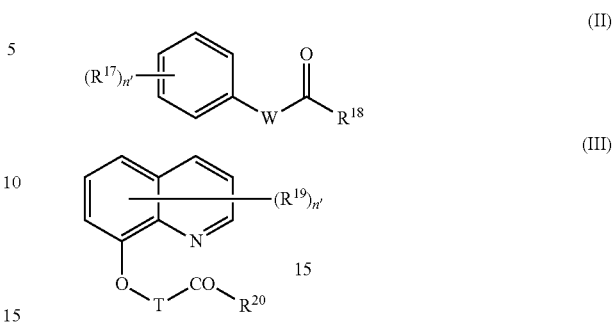

wherein:
n' is an integer from zero to 5, preferably zero to 3;
T is a ($C_1$ or $C_2$)-alkanediyl chain which is unsubstituted or substituted by one or two ($C_1$-$C_4$)-alkyl radicals or by [($C_1$-$C_3$)-alkoxy]carbonyl;
W is an unsubstituted or substituted divalent heterocyclic radical selected from the group of the partially unsaturated or aromatic five-membered heterocyclic rings which have 1 to 3 hetero ring atoms of the N or O type, where the ring contains at least one N atom and not more than one O atom, preferably a radical selected from the group consisting of (W1) to (W4),

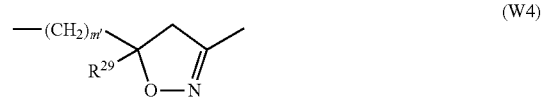

m' is zero or 1;
$R^{17}$ and $R^{19}$ are the same or different halogen, ($C_1$-$C_4$)-alkyl, ($C_1$-$C_4$)-alkoxy, nitro or ($C_1$-$C_4$)-haloalkyl;
$R^{18}$ and $R^{20}$ are the same or different $OR^{24}$, $SR^{24}$ or $NR^{24}R^{25}$ or a saturated or unsaturated 3- to 7-membered heterocycle having at least one N atom and up to 3 hetero atoms, preferably from the group selected from O and S, which is linked to the carbonyl group in (II) or (III) via the N atom and is unsubstituted or substituted by radicals selected from the group consisting of ($C_1$-$C_4$)-alkyl, ($C_1$-$C_4$)-alkoxy or optionally substituted phenyl, preferably a radical of the formula $OR^{24}$, $NHR^{25}$ or $N(CH_3)_2$, in particular of the formula $OR^{24}$;
$R^{24}$ is hydrogen or an unsubstituted or substituted aliphatic hydrocarbon radical, preferably having a total of 1 to 18 C atoms;

$R^{25}$ is hydrogen, $(C_1-C_6)$-alkyl, $(C_1-C_6)$-alkoxy or substituted or unsubstituted phenyl;

$R^{26}$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkyl-silyl; and $R^{27}$, $R^{28}$, $R^{29}$ are the same or different hydrogen, $(C_1-C_8)$-alkyl, $(C_1-C_8)$-haloalkyl, $(C_3-C_{12})$-cycloalkyl or substituted or unsubstituted phenyl;

b) one or more compounds selected from:
4,6-dichloro-2-phenylpyrimidine (fenclorim),
benzyl 2-chloro-4-trifluoromethyl-1,3-thiazole-5-carboxylate (flurazole),
N-(4-methylphenyl)-N'-(1-methyl-1-phenylethyl)urea (daimuron),
1-[4-(N-2-methoxybenzoylsulfamoyl)phenyl]-3-methylurea,
1-[4-(N-2-methoxybenzoylsulfamoyl)phenyl]-3,3-dimethylurea,
1-[4-(N-4,5-dimethylbenzoylsulfamoyl)phenyl]-3-methylurea,
1-[4-(N-naphthoylsulfamoyl)phenyl]-3,3-dimethylurea; or
(2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor)
and their salts and esters, preferably $(C_1-C_8)$; or
(±)-4-dichloroacetyl-3,4-dihydro-3-methyl-2H-1,4-benzoxazine (benoxacor),
N,N-diallyl-2,2-dichloroacetamide(dichlormid),
(RS)-3-dichloroacetyl-5-(2-furyl)-2,2-dimethyloxazolidine (furilazole),
N-(4-chlorophenyl)maleimide(CMPI),
4-hydroxy-1-methyl-3-(1-1H-tetrazol-5-ylmethanoyl)-1H-quinolin-2-one,
(S)-1-(1-alpha-methylbenzyl)-3-p-tolylurea ((S)-MBU), and
S-1-methyl-1-phenylethyl piperidine-1-carbothioate (dimepiperate).

c) N-acylsulfonamides of the formula (IV) or salts thereof:

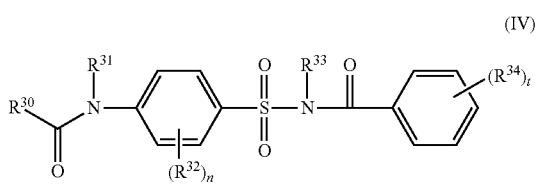

(IV)

wherein:
$R^{30}$ is hydrogen; or $R^{30}$ is a hydrocarbon radical, a hydrocarbon-oxy radical, a hydrocarbon-thio radical or a heterocyclyl radical which is preferably bonded via a carbon atom, which radicals are unsubstituted or substituted by one or more groups selected from halogen, cyano, nitro, amino, hydroxyl, carboxyl, formyl, carboxamide, sulfonamide and radicals of the formula $Z^e-R^a$, each hydrocarbon moiety preferably having 1 to 20 carbon atoms and a carbon-containing radical $R^{30}$ inclusive of substituents preferably having 1 to 30 carbon atoms;

$R^{31}$ is hydrogen or $(C_1-C_4)$-alkyl, preferably hydrogen, or
$R^{30}$ and $R^{31}$ together with the group of the formula —CO—N— are the residue of a 3- to 8-membered saturated or unsaturated ring;

$R^{32}$ is identical or different halogen, cyano, nitro, amino, hydroxyl, carboxyl, formyl, $CONH_2$, $SO_2NH_2$ or a radical of the formula $Z^b-R^b$;

$R^{33}$ is hydrogen or $(C_1-C_4)$-alkyl, preferably H;

$R^{34}$ is the same or different halogen, cyano, nitro, amino, hydroxyl, carboxyl, CHO, $CONH_2$, $SO_2NH_2$ or a radical of the formula $Z^c-R^c$;

$R^a$ is a hydrocarbon radical or a heterocyclyl radical, which radicals are unsubstituted or substituted by one or more groups which may be the same or different selected from halogen, cyano, nitro, amino, hydroxyl, mono- and di-$[(C_1-C_4)$-alkyl]amino, or an alkyl radical in which a plurality, preferably 2 or 3, non-adjacent $CH_2$ groups are in each case replaced by one oxygen atom;

$R^b$ and $R^c$ are the same or different hydrocarbon radical or heterocyclyl radical, which radicals are unsubstituted or substituted by one or more groups which may be the same or different selected from halogen, cyano, nitro, amino, hydroxyl, phosphoryl, halo-$(C_1-C_4)$-alkoxy, mono- and di-$[(C_1-C_4)$-alkyl]amino, or an alkyl radical in which a plurality, preferably 2 or 3, non-adjacent $CH_2$ groups are replaced in each case by one oxygen atom;

$Z^a$ is a divalent group of the formula O, S, CO, CS, CO—O, CO—S, O—CO, —S—CO, SO, $SO_2$, NR*, CO—NR*, NR*—CO, $SO_2$—NR* or NR*—$SO_2$, the bond given on the right-hand side of each of the divalent groups being the bond to the radical $R^a$, and the radicals R* are each independently H, $(C_1-C_4)$-alkyl or halo-$(C_1-C_4)$-alkyl;

$Z^b$ and $Z^c$ are each independently a direct bond or a divalent group of the formula O, S, CO, CS, CO—O, CO—S, O—CO, S—CO, SO, $SO_2$, NR*, $SO_2$—NR*, NR*—$SO_2$, CO—NR* or NR*—CO, where, in asymmetrical divalent groups, the atom on the right-hand side is linked to the radical $R^b$ or $R^c$ and where the radicals R* are each independently H, $(C_1-C_4)$-alkyl or halo-$(C_1-C_4)$-alkyl;

n is an integer from zero to 4, preferably zero, 1 or 2, in particular zero or 1, and t is an integer from zero to 5, preferably zero, 1, 2 or 3, in particular zero, 1 or 2;

d) acylsulfamoylbenzamides of the formula (V), or salts thereof:

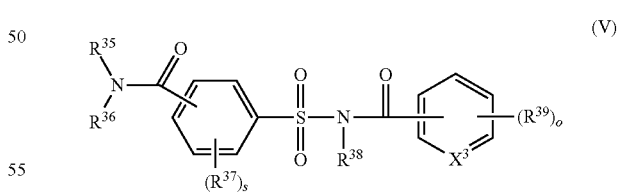

(V)

wherein:
$X^3$ is CH or N;

$R^{35}$ is hydrogen, or a heterocyclyl or hydrocarbon radical, which radicals are optionally substituted by one or more groups which may be the same or different selected from halogen, cyano, nitro, amino, hydroxyl, carboxyl, CHO, $CONH_2$, $SO_2NH_2$ and $Z^d-R^d$;

$R^{36}$ is hydrogen, hydroxyl; or $R^{36}$ is $(C_1-C_6)$-alkyl, $(C_2-C_6)$-alkenyl, $(C_2-C_6)$-alkynyl, $(C_1-C_6)$-alkoxy, $(C_2-C_6)$-alkenyloxy, which radicals are optionally substituted by one or more groups which may be the same or different selected from halogen, hydroxyl, (C, —CA)-alkyl, ($C_1$-$C_4$)-alkoxy and ($C_1$-$C_4$)-alkylthio, or $R^{35}$ and $R^{36}$ together with the nitrogen atom to which they are attached are a 3- to 8-membered saturated or unsaturated ring;

$R^{37}$ is halogen, cyano, nitro, amino, hydroxyl, carboxyl, CHO, $CONH_2$, $SO_2NH_2$ or $Z^e$-$R^e$;

$R^{38}$ is hydrogen, ($C_1$-$C_4$)-alkyl, ($C_2$-$C_4$)-alkenyl or ($C_2$-$C_4$)-alkynyl;

$R^{39}$ is halogen, cyano, nitro, amino, hydroxyl, carboxyl, phosphoryl, CHO, $CONH_2$, $SO_2NH_2$ or $Z^f$-$R^f$;

$R^d$ is a ($C_2$-$C_{20}$)-alkyl radical whose carbon chain is interrupted by one or more oxygen atoms; or $R^d$ is a heterocyclyl or a hydrocarbon radical, which radicals are optionally substituted by one or more groups which may be the same or different selected from halogen, cyano, nitro, amino, hydroxyl, mono- and di-[($C_1$-$C_4$)-alkyl]amino;

$R^e$ and $R^f$ are the same or different ($C_2$-$C_{20}$)-alkyl radical which carbon chain is interrupted by one or more oxygen atoms; or $R^e$ and $R^f$ are the same or different heterocyclyl or hydrocarbon radical, which radicals are optionally substituted by one or more groups which may be the same or different selected from halogen, cyano, nitro, amino, hydroxyl, phosphoryl, ($C_1$-$C_4$)-haloalkoxy, mono- and di-[($C_1$-$C_4$)-alkyl]amino;

$Z^d$ is a divalent unit selected from the group consisting of O, S, CO, CS, C(O)O, C(O)S, SO, $SO_2$, NR*, C(O)NR— or $SO_2NR*$;

$Z^e$ and $Z^f$ are the same or different and are a direct bond or a divalent unit selected from O, S, CO, CS, C(O)O, C(O)S, SO, $SO_2$, NR*, $SO_2NR*$ and C(O)NR*;

R* is hydrogen, ($C_1$-$C_4$)-alkyl or ($C_1$-$C_4$)-haloalkyl;

s is an integer from zero to 4, and o is an integer from zero to 5 when X is CH, or is an integer from zero to 4 when X is N;

e) compounds of the formula (VI):

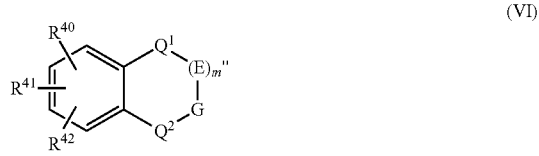

(VI)

wherein:

$R^{40}$ is H, ($C_1$-$C_4$)-alkyl, ($C_1$-$C_4$)-alkyl substituted by ($C_1$-$C_4$)-alkyl-$X^4$ or ($C_1$-$C_4$)— haloalkyl-$X^4$, ($C_1$-$C_4$)-haloalkyl, $NO_2$, CN, —COO—$R^{43}$, $NR_2^{44}$, $SO_2NR_2^{45}$ or $CONR_2^{46}$;

$R^{41}$ is H, halogen, ($C_1$-$C_4$)-alkyl, $CF_3$, ($C_1$-$C_4$)-alkoxy or ($C_1$-$C_4$)-haloalkoxy;

$R^{42}$ is H, halogen or ($C_1$-$C_4$)-alkyl;

$Q^1$, $Q^2$, E and G are the same or different O, S, $CR_2^{47}$, CO, $NR^{48}$ or a group of the formula (VII):

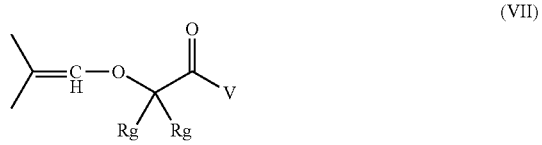

(VII)

with the proviso that:

i) at least one of the groups $Q^1$, $Q^2$, E, G is a carbonyl group, that exactly one of these groups is a radical of the formula (VII) and that the group of the formula (VII) is adjacent to a carbonyl group, and ii) two adjacent groups $Q^1$, $Q^2$, E and G cannot simultaneously be oxygen;

$R^g$ is the same or different H or ($C_1$-$C_8$)-alkyl or the two radicals $R^g$ together are ($C_2$-$C_6$)-alkylene;

V is $Y^3$—$R^h$ or $NR_2^{49}$;

$X^4$ is O or $S(O)_l$;

$Y^3$ is O or S;

$R^h$ is H, ($C_1$-$C_8$)-alkyl, ($C_1$-$C_8$)-haloalkyl, ($C_1$-$C_4$)-alkoxy-($C_1$-$C_8$)-alkyl, ($C_3$-$C_6$)— alkenyloxy-($C_1$-$C_9$)-alkyl, or phenyl-($C_1$-$C_8$)-alkyl, where the phenyl ring is optionally substituted by halogen, ($C_1$-$C_4$)-alkyl, $CF_3$, methoxy or methyl-$S(O)_x$; ($C_3$-$C_6$)alkenyl, ($C_3$-$C_6$)-haloalkenyl, phenyl-($C_3$-$C_6$)-alkenyl, ($C_3$-$C_6$)-alkynyl, phenyl-($C_3$-$C_6$)-alkynyl, oxetanyl, furfuryl or tetrahydrofuryl;

$R^{43}$ is H or ($C_1$-$C_4$)-alkyl;

$R^{44}$ is H, ($C_1$-$C_4$)-alkyl, ($C_1$-$C_4$)-alkylcarbonyl or the two radicals $R^{44}$ together are ($C_4$-$C_5$)-alkylene;

$R^{45}$ and $R^{46}$ are the same or different H, ($C_1$-$C_4$)-alkyl, or the two radicals $R^{45}$ and/or $R^{46}$ together are ($C_4$-$C_5$)-alkylene, where one $CH_2$ group can be replaced by O or S or one or two $CH_2$ groups can be replaced by $NR^i$;

$R^i$ is H or ($C_1$-$C_8$)-alkyl;

$R^{47}$ is H, ($C_1$-$C_8$)-alkyl or the two radicals $R^{47}$ together are ($C_2$-$C_6$)-alkylene;

$R^{48}$ is H, ($C_1$-$C_8$)-alkyl, substituted or unsubstituted phenyl, or benzyl which is unsubstituted or substituted on the phenyl ring;

$R^{49}$ is H, ($C_1$-$C_8$)-alkyl, phenyl, phenyl-($C_1$-$C_8$)-alkyl, which phenyl rings can be substituted by F, Cl, Br, $NO_2$, CN, $OCH_3$, ($C_1$-$C_4$)-alkyl or $CH_3SO_2$—; ($C_1$-$C_4$)-alkoxy-($C_1$-$C_8$)-alkyl, ($C_3$-$C_6$)-alkenyl, ($C_3$-$C_6$)-alkynyl, ($C_3$-$C_6$)-cycloalkyl or two radicals $R^{49}$ together are ($C_4$-$C_5$)-alkylene, where one $CH_2$ group can be replaced by O or S or one or two $CH_2$ groups can be replaced by $NR^k$;

$R^k$ is H or ($C_1$-$C_4$)-alkyl;

m" is 0 or 1 and l is 0, 1 or 2;

including stereoisomers and agriculturally acceptable salts.

Unless otherwise defined individually, the following definitions generally apply to the radicals in the formulae (II) to (VII).

The radicals alkyl, alkoxy, haloalkyl, haloalkoxy, alkylamino and alkylthio and the corresponding unsaturated and/or substituted radicals can be in each case straight-chain or branched in the carbon skeleton. Alkyl radicals, also the composite meanings such as alkoxy, haloalkyl and the like, preferably have 1 to 4 carbon atoms and are, for example, methyl, ethyl, n- or i-propyl or n-, i-, t- or 2-butyl. Alkenyl and alkynyl radicals have the meanings of the unsaturated radicals which are possible which correspond to the alkyl radicals; alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl is, for example, propargyl, but-2-yn-1-yl, but-3-yn-1-yl, 1-methylbut-3-yn-1-yl. "($C_1$-$C_4$)-Alkyl" is the abbreviation for alkyl having 1 to 4 carbon atoms; the same applies analogously to other general definitions of radicals, where the range of the possible number of carbon atoms is indicated in brackets.

Cycloalkyl is, preferably, a cyclic alkyl radical having 3 to 8, preferably 3 to 7, especially preferably 3 to 6, carbon atoms, for example cyclopropyl, cyclobutyl, cyclopentyl and cyclohexyl. Cycloalkenyl and cycloalkinyl denote corresponding unsaturated compounds.

Halogen is fluorine, chlorine, bromine or iodine. Haloalkyl, haloalkenyl and haloalkynyl are alkyl, alkenyl or alkynyl which are partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$.

Haloalkoxy is, for example, $OCF_3$, $OCHF_2$, $OCH_2F$, $CF_3CF_2O$, $OCH_2CF_3$ and $OCH_2CH_2Cl$. This also applies analogously to other halogen-substituted radicals. A hydrocarbon radical can be an aromatic or an aliphatic hydrocarbon radical, where an aliphatic hydrocarbon radical is generally a straight-chain or branched saturated or unsaturated hydrocarbon radical, preferably having 1 to 18, especially preferably 1 to 12, carbon atoms, for example alkyl, alkenyl or alkynyl.

Aliphatic hydrocarbon radical preferably means alkyl, alkenyl or alkynyl having up to 12 carbon atoms; the same applies analogously to an aliphatic hydrocarbon radical in a hydrocarbon-oxy radical.

Aryl is generally a mono-, bi- or polycyclic aromatic system having by preference 6-20 carbon atoms, preferably 6 to 14 carbon atoms, especially preferably 6 to 10 carbon atoms, for example phenyl, naphthyl, tetrahydronaphthyl, indenyl, indanyl, pentalenyl and fluorenyl, especially preferably phenyl.

Heterocyclic ring, heterocyclic radical or heterocyclyl is a mono-, bi- or polycyclic ring system which is saturated, unsaturated and/or aromatic and contains one or more, preferably 1 to 4, hetero atoms, preferably selected from the group consisting of N, S and O.

Preferred are saturated heterocycles having 3 to 7 ring atoms and one or two hetero atoms selected from the group consisting of N, O and S, their chalcogens not being adjacent. Especially preferred are monocyclic rings having 3 to 7 ring atoms and a hetero atom selected from the group consisting of N, O and S, and also morpholine, dioxolane, piperazine, imidazoline and oxazolidine. Very especially preferred saturated heterocycles are oxirane, pyrrolidone, morpholine and tetrahydrofuran.

Also preferred are partially unsaturated heterocycles having 5 to 7 ring atoms and one or two hetero atoms selected from the group consisting of N, O and S.

Especially preferred are partially unsaturated heterocycles having 5 to 6 ring atoms and one hetero atom selected from the group consisting of N, O and S. Very especially preferred partially unsaturated heterocycles are pyrazoline, imidazoline and isoxazoline.

Equally preferred is heteroaryl, for example mono- or bicyclic aromatic heterocycles having 5 to 6 ring atoms which contain one to four hetero atoms selected from the group consisting of N, O, S, the chalcogens not being adjacent. Especially preferred are monocyclic aromatic heterocycles having 5 to 6 ring atoms which contains a hetero atom selected from the group consisting of N, O and S, and also pyrimidine, pyrazine, pyridazine, oxazole, thiazole, thiadiazole, oxadiazole, pyrazole, triazole and isoxazole. Very especially preferred are pyrazole, thiazole, triazole and furan.

Substituted radicals, such as substituted hydrocarbon radicals, for example substituted alkyl, alkenyl, alkynyl, aryl such as phenyl and arylalkyl such as benzyl, or substituted heterocyclyl, are a substituted radical which is derived from an unsubstituted skeleton, the substituents being, by preference, one or more, by preference 1, 2 or 3, in the case of Cl and F also up to the maximum possible number of, substituents selected from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino such as acylamino, mono- and dialkylamino and alkylsulfynyl, haloalkylsulfynyl, alkylsulfonyl, haloalkylsulfonyl and, in the case of cyclic radicals, also alkyl and haloalkyl and the unsaturated aliphatic substituents which correspond to the abovementioned saturated hydrocarbon-containing substituents, preferably alkenyl, alkynyl, alkenyloxy and alkynyloxy. In the case of radicals having carbon atoms, those having 1 to 4 carbon atoms, in particular 1 or 2 carbon atoms, are preferred. As a rule, preferred substituents are those seelected from the group consisting of halogen, for example fluorine or chlorine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano. Especially preferred in this context are the substituents methyl, methoxy and chlorine.

Mono- or disubstituted amino is a chemically stable radical selected from the group of the substituted amino radicals which are N-substituted by, for example, one or two identical or different radicals selected from the group consisting of alkyl, alkoxy, acyl and aryl; preferably monoalkylamino, dialkylamino, acylamino, arylamino, N-alkyl-N-arylamino and N-heterocycles. Preferred in this context are alkyl radicals having 1 to 4 carbon atoms. By preference, aryl is phenyl. By preference, substituted aryl is substituted phenyl. The definition given further below applies to acyl, preferably $(C_1-C_4)$-alkanoyl. This also applies analogously to substituted hydroxylamino or hydrazino.

By preference, optionally substituted phenyl is phenyl which is unsubstituted or mono- or polysubstituted, preferably up to trisubstituted, in the case of halogen such as Cl and F also up to pentasubstituted, by identical or different radicals selected from the group consisting of halogen, $(C_1-C_4)$-alkyl, $(C_1-C_4)$-alkoxy, $(C_1-C_4)$-haloalkyl, $(C_1-C_4)$-haloalkoxy and nitro, for example o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

An acyl radical is the radical of an organic acid having by preference up to 6 carbon atoms, for example the radical of a carboxylic acid and radicals of acids derived therefrom, such as thiocarboxylic acid, optionally N-substituted iminocarboxylic acids, or the radical of carbonic monoesters, optionally N-substituted carbamic acids, sulfonic acid, sulfinic acids, phoshonic acids, phosphinic acids. Acyl is, for example, formyl, alkylcarbonyl such as $(C_1-C_4$-alkyl)-carbonyl, phenylcarbonyl, it being possible for the phenyl ring to be substituted, for example as indicated above for phenyl, or alkyloxycarbonyl, phenyloxycarbonyl, benzyloxycarbonyl, alkylsulfonyl, alkylsulfynyl or N-alkyl-1-iminoalkyl.

Formulae (II) to (VII) are also understood to include all stereoisomers and mixtures thereof. The stereoisomers include enantiomers, diastereomers and Z- and E-isomers.

Preferred herbicide/antidote combinations are those which comprise antidotes of the formula (II) and/or (III) where the symbols and indices have the following meanings:

$R^{24}$ is hydrogen, $(C_1-C_{18})$-alkyl, $(C_3-C_{12})$-cycloalkyl, $(C_2-C_8)$-alkenyl and $(C_2-C_{18})$-alkynyl, where the carbon-containing groups can be substituted by one or more preferably up to three, radicals $R^{50}$;

$R^{50}$ is the same or different halogen, hydroxyl, $(C_1-C_8)$-alkoxy, $(C_1-C_8)$-alkylthio, $(C_2-C_8)$-alkenylthio, $(C_2-C_8)$-alkynylthio, $(C_2-C_8)$-alkenyloxy, $(C_2-C_8)$-alkynyloxy, $(C_3-C_7)$-cycloalkyl, $(C_3-C_7)$-cycloalkoxy, cyano, mono- and di-$(C_1-C_4)$-alkyl)amino, carboxyl, $(C_1-C_8)$-alkoxycarbonyl, $(C_2-C_8)$-alkenyloxycarbonyl, $(C_1-C_8)$-alkylthiocarbonyl, $(C_2-C_8)$-alkynyloxycarbonyl, $(C_1-C_8)$-alkylcarbonyl, $(C_2-C_8)$-alkenylcarbonyl, $(C_2-C_{18})$-alkynylcarbonyl, 1-(hydroxyimino)-$(C_1-C_6)$-alkyl, 1-[$(C_1-C_4)$-alkylimino]-$(C_1-C_4)$-alkyl, 1-[$(C_1-C_4)$-alkoxyimino]-$(C_1-C_6)$-alkyl, $(C_1-C_8)$-alkylcarbonylamino, $(C_2-C_8)$-alkenylcarbonylamino, $(C_2-C_8)$-alkynylcarbonylamino, aminocarbonyl, $(C_1-C_8)$-alkylaminocarbonyl, di-$(C_1-C_6)$-alkylaminocarbonyl, $(C_2-C_6)$-alkenylaminocarbonyl, $(C_2-C_6)$-alkynylaminocarbonyl, $(C_1-C_8)$-alkoxycarbonylamino, $(C_1-C_8)$-alkylaminocarbonylamino, $(C_1-C_6)$-alkylcarbonyloxy which is unsubstituted or substituted by $R^{51}$, or is $(C_2-C_6)$-alkenylcarbonyloxy, $(C_2-C_6)$-alkynylcarbonyloxy, $(C_1-C_8)$-alkylsulfonyl, phenyl, phenyl-$(C_1-C_6)$-alkoxy, phenyl-$(C_1-C_6)$-alkoxycarbonyl, phenoxy, phenoxy-$(C_1-C_6)$-alkoxy, phenoxy-$(C_1-C_6)$-alkoxycarbonyl, phenylcarbonyloxy, phenylcarbonylamino, phenyl-$(C_1-C_6)$-alkylcarbonylamino, it being possible for the last-mentioned 9 radicals to be unsubstituted or mono- or polysubstituted, preferably up to trisubstituted, by radicals $R^{52}$; SiR'$_3$, OSiR'$_3$, R'$_3$Si—$(C_1-C_8)$-alkoxy, CO—O—NR'$_2$, O—N=CR'$_2$, N=CR'$_2$, O—N R'$_2$, NR'$_2$, CH(OR')$_2$, O—$(CH_2)_q$—CH(OR')$_2$, CR''' (OR')$_2$, O—$(CH_2)_w$CR''' (OR'')$_2$ or by R''O—CHR'''CHCOR''—$(C_1-C_6)$-alkoxy, $R^{51}$ is the same or different halogen, nitro, $(C_1-C_4)$-alkoxy and phenyl which is unsubstituted or substituted by one or more, preferably up to three, radicals $R^{52}$;

$R^{52}$ is the same or different halogen, $(C_1-C_4)$-alkyl, $(C_1-C_4)$-alkoxy, $(C_1-C_4)$-haloalkyl, $(C_1-C_4)$-haloalkoxy or nitro;

R' is the same or different hydrogen, $(C_1-C_4)$-alkyl, phenyl which is unsubstituted or substituted by one or more, preferably up to three, radicals $R^{52}$, or two radicals R' together form a $(C_2-C_6)$-alkanediyl chain;

R'' is the same or different $(C_1-C_4)$-alkyl or two radicals R'' together form a $(C_2-C_6)$— alkanediyl chain;

R''' is hydrogen or $(C_1-C_4)$-alkyl; and w is zero, 1, 2, 3, 4, 5 or 6.

Especially preferred are herbicide/antidote combinations according to the invention which comprise antidotes of the formula (II) and/or (III) where the symbols and indices have the following meanings:

$R^{24}$ is hydrogen, $(C_1-C_8)$-alkyl or $(C_3-C_7)$-cycloalkyl, the above carbon-containing radicals being unsubstituted or mono- or polysubstituted by halogen or mono- or disubstituted, by preference monosubstituted, by radicals $R^{50}$, $R^{50}$ is the same or different hydroxyl, $(C_1-C_4)$-alkoxy, carboxyl, $(C_1-C_4)$-alkoxycarbonyl, $(C_2-C_6)$-alkenyloxycarbonyl, $(C_2-C_6)$-alkynyloxycarbonyl, 1-(hydroxyimino)-$(C_1-C_4)$-alkyl, 1-[$(C_1-C_4)$-alkylimino]-$(C_1-C_4)$-alkyl and 1-[$(C_1-C_4)$— alkoxyimino]-$(C_1-C_4)$-alkyl; SiR'$_3$, O—N=CR'$_2$, N=CR'$_2$, NR'$_2$ and ONR'$_3$ where R' is identical or different hydrogen, $(C_1-C_4)$-alkyl or, as a pair, a $(C_4-C_5)$-alkanediyl chain, $R^{27}$, $R^{28}$ and $R^{29}$ are the same or different hydrogen, $(C_1-C_8)$-alkyl, $(C_1-C_6)$-haloalkyl, $(C_3-C_7)$-cycloalkyl or phenyl which is unsubstituted or substituted by one or more groups selected from halogen, cyano, nitro, amino, mono- and di-[$(C_1-C_4)$-alkyl]-amino, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio and $(C_1-C_4)$-alkylsulfonyl;

$R^{26}$ is hydrogen, $(C_1-C_8)$-alkyl, $(C_1-C_8)$-haloalkyl, $(C_1-C_4)$-alkoxy)-$(C_1-C_4)$-alkyl, $(C_1-C_6)$— hydroxyalkyl, $(C_3-C_7)$-cycloalkyl or tri-$(C_1-C_4)$-alkylsilyl, $R^{17}$ and $R^{19}$ are the same or different halogen, methyl, ethyl, methoxy, ethoxy, $(C_1$ or $C_2)$-haloalkyl, by preference hydrogen, halogen or $(C_1$ or $C_2)$-haloalkyl.

Very especially preferred are antidotes in which the symbols and indices in formula (II) have the following meanings:

$R^{17}$ is halogen, nitro or $(C_1-C_4)$-haloalkyl;

n' is zero, 1, 2 or 3;

$R^{18}$ is a radical of the formula $OR^{24}$, $R^{24}$ is hydrogen, $(C_1-C_8)$-alkyl or $(C_3-C_7)$-cycloalkyl, where the above carbon-containing radicals are unsubstituted or mono- or polysubstituted, by preference up to trisubstituted, by the same or different halogen radicals, or up to disubstituted, by preference monosubstituted, by identical or different radicals selected from the group consisting of hydroxyl, $(C_1-C_4)$-alkoxy, $(C_1-C_4)$-alkoxycarbonyl, $(C_2-C_6)$-alkenyloxycarbonyl, $(C_2-C_6)$-alkynyloxycarbonyl, 1-(hydroxyimino)-$(C_1-C_4)$-alkyl, 1-[$(C_1-C_4)$-alkylimino]-$(C_1-C_4)$-alkyl, 1-[$(C_1-C_4)$-alkoxyimino]-$(C_1-C_4)$-alkyl and radicals of the formulae SiR'$_3$, O—N=CR'$_2$, N=CR'$_2$, NR'$_2$ and O—NR'$_2$, where the radicals R' in the abovementioned formulae are identical or different hydrogen, $(C_1-C_4)$-alkyl or, as a pair, are $(C_4$ or $C_5)$-alkanediyl;

$R^{27}$, $R^{28}$ and $R^{29}$ are the same or different hydrogen, $(C_1-C_8)$-alkyl, $(C_1-C_6)$-haloalkyl, $(C_3-C_7)$-cycloalkyl or phenyl which is unsubstituted or substituted by one or more radicals selected from halogen, $(C_1-C_4)$-alkyl, $(C_1-C_4)$-alkoxy, nitro, $(C_1-C_4)$-haloalkyl and $(C_1-C_4)$-haloalkoxy, and $R^{26}$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_7)$-cycloalkyl or tri-$(C_1-C_4)$-alkylsilyl.

Very especially preferred are also antidotes of the formula (111) where the symbols and indices have the following meanings:

$R^{19}$ is halogen or $(C_1-C_4)$-haloalkyl;

n' is zero, 1, 2 or 3, where $(R^{19})_{n'}$ is, by preference, 5-Cl;

$R^{20}$ is a radical of the formula $OR^{24}$;

T is $CH_2$ or $CH(COO$—$(C_1-C_3)$-alkyl), and $R^{24}$ is hydrogen, $(C_1-C_8)$-alkyl, $(C_1-C_8)$-haloalkyl or $(C_1-C_4)$-alkoxy-$(C_1-C_4)$-alkyl, by preference $(C_1-C_8)$-alkyl.

Especially preferred are antidotes of the formula (II) where the symbols and indices have the following meanings:

W is (W1);

$R^{17}$ is halogen or $(C_1-C_2)$-haloalkyl;

n' is zero, 1, 2 or 3, where $(R^{17})_{n'}$ is by preference 2,4-$Cl_2$;

$R^{18}$ is a radical of the formula $OR^{24}$;

$R^{24}$ is hydrogen, $(C_1-C_8)$-alkyl, $(C_1-C_4)$-haloalkyl, $(C_1-C_4)$-hydroxyalkyl, $(C_3-C_7)$-cycloalkyl, $(C_1-C_4)$-alkoxy-$(C_1-C_4)$-alkyl or tri-$(C_1-C_2)$-alkylsilyl, by preference $(C_1-C_4)$-alkyl;

$R^{27}$ is hydrogen, $(C_1-C_8)$-alkyl, $(C_1-C_4)$-haloalkyl or $(C_3-C_7)$-cycloalkyl, by preference hydrogen or $(C_1-C_4)$-alkyl, and $R^{26}$ is hydrogen, $(C_1-C_8)$-alkyl, $(C_1-C_4)$-haloalkyl, $(C_1-C_4)$-hydroxyalkyl, $(C_3-C_7)$-cycloalkyl, $(C_1-C_4)$-alkoxy-$(C_1-C_4)$-alkyl or tri-$(C_1-C_2)$-alkylsilyl, by preference hydrogen or $(C_1-C_4)$-alkyl.

Also especially preferred are herbicidal compositions comprising an antidote of the formula (II) where the symbols and indices have the following meanings:

W is (W2);

$R^{17}$ is halogen or $(C_1-C_2)$-haloalkyl;

n' is zero, 1, 2 or 3, where $(R^7)_n$ is by preference 2,4-$C_{12}$;

$R^{18}$ is a radical of the formula $OR^{24}$;

$R^{24}$ is hydrogen, $(C_1-C_8)$-alkyl, $(C_1-C_4)$-haloalkyl, $(C_1-C_4)$-hydroxyalkyl, $(C_3-C_7)$-cycloalkyl, $(C_1-C_4$-alkoxy)-$(C_1-C_4)$-alkyl or tri-$(C_1-C_2)$-alkyl-silyl, by preference $(C_1-C_4)$-alkyl, and $R^{27}$ is hydrogen, $(C_1-C_8)$-alkyl, $(C_1-C_4)$-haloalkyl, $(C_3-C_7)$-cycloalkyl or phenyl, by preference hydrogen or $(C_1-C_4)$-alkyl.

Also especially preferred are antidotes of the formula (II) where the symbols and indices have the following meanings:

W is (W3);
$R^{17}$ is halogen or $(C_1-C_2)$-haloalkyl;
n' is zero, 1, 2 or 3, where $(R^{17})_n$ is by preference 2,4-$Cl_2$;
$R^{18}$ is a radical of the formula $OR^{24}$;
$R^{24}$ is hydrogen, $(C_1-C_8)$-alkyl, $(C_1-C_4)$-haloalkyl, $(C_1-C_4)$-hydroxyalkyl, $(C_3-C_7)$-cycloalkyl, $(C_1-C_4)$-alkoxy-$(C_1-C_4)$-alkyl or tri-$(C_1-C_2)$-alkylsilyl, by preference $(C_1-C_4)$-alkyl, and
$R^{28}$ is $(C_1-C_8)$-alkyl or $(C_1-C_4)$-haloalkyl, by preference $C_1$-haloalkyl.

Also especially preferred are antidotes of the formula (II) where the symbols and indices have the following meaning:
W is (W4);
$R^{17}$ is halogen, nitro, $(C_1-C_4)$-alkyl, $(C_1-C_2)$-haloalkyl, by preference $CF_3$, or $(C_1-C_4)$—alkoxy;
n' is 0, 1, 2 or 3;
m' is 0 or 1;
$R^{18}$ is a radical of the formula $OR^{24}$;
$R^{24}$ is hydrogen, $(C_1-C_4)$-alkyl, carboxy-$(C_1-C_4)$-alkyl, $(C_1-C_4)$-alkoxycarbonyl-$(C_1-C_4)$-alkyl, by preference $(C_1-C_4)$-alkoxy-CO—$CH_2$—, $(C_1-C_4)$-alkoxy-CO—C($CH_3$)(H)—, HO—CO—$CH_2$— or HO—CO—C($CH_3$)(H)—, and
$R^{29}$ is hydrogen, $(C_1-C_4)$-alkyl, $(C_1-C_4)$-haloalkyl, $(C_3-C_7)$-cycloalkyl or phenyl which is unsubstituted or substituted by one or more groups selected from halogen, $(C_1-C_4)$-alkyl, $(C_1-C_4)$-haloalkyl, nitro, cyano and $(C_1-C_4)$-alkoxy.

The following groups of compounds are especially suitable for use as antidotes for the herbicidally active substances of the formula (I):
a) compounds of the dichlorophenylpyrazoline-3-carboxylic acid type (i.e. of the formula (II), where W=(W1) and $(R^{17})_n$=2,4-$Cl_2$), by preference compounds such as ethyl 1-(2,4-dichlorophenyl)-5-(ethoxycarbonyl)-5-methyl-2-pyrazoline-3-carboxylate (II-1), and related compounds as described in WO-A 91/07874;
b) dichlorophenylpyrazolecarboxylic acid derivatives (i.e. of the formula (II), where W=(W2) and $(R^{17})_n$=2,4-$Cl_2$), by preference compounds such as ethyl 1-(2,4-dichlorophenyl)-5-methyl-pyrazole-3-carboxylate (II-2), ethyl 1-(2,4-dichlorophenyl)-5-isopropylpyrazole-3-carboxylate (II-3), ethyl 1-(2,4-dichlorophenyl)-5-(1,1-dimethylethyl)pyrazole-3-carboxylate (II-4), ethyl 1-(2,4-dichlorophenyl)-5-phenylpyrazole-3-carboxylate (II-5) and related compounds as described in EP-A-0 333 131 and EP-A-O 269 806.
c) Compounds of the triazolecarboxylic type (i.e. of the formula (III), where W=(W3) and $(R^{17})_n$=2,4-$Cl_2$), by preference compounds such as fenchlorazole ethyl, i.e. ethyl 1-(2,4-dichlorophenyl)-5-trichloromethyl-(1H)-1,2,4-triazole-3-carboxylate (II-6); fenchlorazole, i.e. 1-(2,4-dichlorophenyl)-5-trichloromethyl-(1H)-1,2,4-triazole-3-carboxylic acid, and related compounds (see EP-A-0 174 562 and EP-A-0 346 620);
d) Compounds of the 5-benzyl- or 5-phenyl-2-isoxazoline-3-carboxylic acid type or the 5,5-diphenyl-2-isoxazoline-3-carboxylic acid type (where W=(W4)), by preference compounds such as ethyl 5-(2,4-dichlorobenzyl)-2-isoxazoline-3-carboxylate (II-7) or ethyl 5-phenyl-2-isoxazoline-3-carboxylate (II-8) and related compounds as they are described in WO-A-91/08202, or ethyl 5,5-diphenyl-2-isoxazoline-3-carboxylate (II-9), or 5,5-diphenyl-2-isoxazoline-3-carboxylic acid, or n-propyl 5,5-diphenyl-2-isoxazoline-carboxylate (II-10) or ethyl 5-(4-fluorophenyl)-5-phenyl-2-isoxazoline-3-carboxylate (II-11), as described in WO-A-95/07897.
e) Compounds of the 8-quinolinoxyacetic acid type, for example those of the formula (III) where $(R^{19})_n$=5-Cl, $R^{20}$=$OR^{24}$ and T=$CH_2$, by preference the compounds
1-methyl(5-chloro-8-quinolinoxy)acetate (III-1),
1,3-dimethyl-but-1-yl(5-chloro-8-quinolinoxy)acetate (III-2),
4-allyloxybutyl(5-chloro-8-quinolinoxy)acetate (III-3),
1-allyloxyprop-2-yl(5-chloro-8-quinolinoxy)acetate (III-4),
ethyl(5-chloro-8-quinolinoxy)acetate (III-5),
methyl(5-chloro-8-quinolinoxy)acetate (III-6),
allyl(5-chloro-8-quinolinoxy)acetate (III-7),
2-(2-propylideneiminoxy)-1-ethyl(5-chloro-8-quinolinoxy) acetate (III-8),
2-oxo-prop-1-yl(5-chloro-8-quinolinoxy)acetate (III-9) and related compounds as they are described in EP-A-0 860 750, EP-A-0 094 349 and EP-A-0 191 736 or EP-A-0 492 366.
f) Compounds of the (5-chloro-8-quinolinoxy)malonic acid type, i.e. of the formula (III) where $(R^{19})_n$=5-Cl, $R^{20}$=$OR^{24}$, T=—CH(COO-alkyl)-, by preference the compounds diethyl(5-chloro-8-quinolinoxy)malonate, diallyl(5-chloro-8-quinolinoxy)malonate, methyl ethyl(5-chloro-8-quinolinoxy)malonate and related compounds as they are described in EP-A-0 582 198.
g) Compounds selected from:
N,N-diallyl-2,2-dichloroacetamide (dichlormid, from U.S. Pat. No. 4,137,070),
4-dichloroacetyl-3,4-dihydro-3-methyl-2H-1,4-benzoxazine (benoxacor, from EP 0 149 974),
3-dichloroacetyl-5-(2-furanyl)-2,2-dimethyloxazolidine (furilazole, MON 13900),
4,6-dichloro-2-phenylpyrimidine (fenclorim),
benzyl 2-chloro-4-trifluoromethyl-1,3-thiazole-5-carboxylate (flurazole),
N-(4-methylphenyl)-N'-(1-methyl-1-phenylethyl)urea (daimuron),
1-[4-(N-2-methoxybenzoylsulfamoyl)phenyl]-3-methylurea,
1-[4-(N-2-methoxybenzoylsulfamoyl)phenyl]-3,3-dimethylurea,
1-[4-(N-4,5-dimethylbenzoylsulfamoyl)phenyl]-3-methylurea,
1-[4-(N-naphthoylsulfamoyl)phenyl]-3,3-dimethylurea,
(2,4-dichlorophenoxy)acetic acid (2,4-D); or
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor),
and their salts and esters, by preference $(C_1-C_8)$; or
N-(4-chlorophenyl)maleimide(CMPI),
4-hydroxy-1-methyl-3-(1-1H-tetrazol-5-ylmethanoyl)-1H-quinolin-2-one,
(S)-1-(1-alpha-methylbenzyl)-3-p-tolylurea ((S)-MBU), and
S-1-methyl-1-phenylethyl piperidine-1-carbothioate (dimepiperate).

Furthermore preferred as antidotes are compounds of the formula (IV) or salts thereof in which:
$R^{30}$ is hydrogen; or $R^{30}$ is $(C_1-C_6)$-alkyl, $(C_3-C_6)$-cycloalkyl, furanyl or thienyl, which radicals are unsubstituted or substituted by one or more groups selected from halogen, ($C_1$-$C_4$)-alkoxy, halo-($C_1$-$C_6$)-alkoxy and ($C_1$-$C_4$)-alkylthio and, in the case of cyclic radicals, also ($C_1$-$C_4$)-alkyl and ($C_1$-$C_4$)-haloalkyl, $R^{31}$ is hydrogen, $R^{32}$ is halogen, halo-($C_1$-$C_4$)-alkyl, halo-($C_1$-$C_4$)-alkoxy, ($C_1$-$C_4$)-alkyl, ($C_1$-$C_4$)-alkoxy, ($C_1$-$C_4$)-alkylsulfonyl, ($C_1$-$C_4$)-alkoxycarbonyl or ($C_1$-$C_4$)-alkylcarbonyl, by preference halogen, ($C_1$-$C_4$)-haloalkyl such as trifluoromethyl, ($C_1$-$C_4$)-alkoxy, halo-($C_1$-$C_4$)-alkoxy, ($C_1$-$C_4$)-alkoxycarbonyl or ($C_1$-$C_4$)-alkylsulfonyl, $R^{33}$ is hydrogen, $R^{34}$ is halogen, ($C_1$-$C_4$)-alkyl, halo-($C_1$-$C_4$)-alkyl, halo-($C_1$-$C_4$)-alkoxy, ($C_3$-$C_6$)-cycloalkyl, phenyl, ($C_1$-$C_4$)-alkoxy, cyano, ($C_1$-$C_4$)-alkylthio, ($C_1$-$C_4$)-alkylsulfynyl, ($C_1$-$C_4$)-alkylsulfonyl, ($C_1$-$C_4$)-alkoxycarbonyl or ($C_1$-$C_4$)-alkylcarbonyl, by preference halogen, ($C_1$-$C_4$)-alkyl, ($C_1$-$C_4$)-haloalkyl such as trifluoromethyl, halo-($C_1$-$C_4$)-alkoxy, ($C_1$-$C_4$)-alkoxy or ($C_1$-$C_4$)-alkylthio, n is zero, 1 or 2 and t is 1 or 2.

Furthermore preferred are antidotes of the formula (V) in which $X^3$ is CH;

$R^{35}$ is hydrogen; or $R^{35}$ is ($C_1$-$C_6$)-alkyl, ($C_3$-$C_6$)-cycloalkyl, ($C_2$-$C_6$)-alkenyl, ($C_5$-$C_6$)-cycloalkenyl, phenyl or 3- to 6-membered heterocyclyl having up to three hetero atoms selected from the group consisting of nitrogen, oxygen and sulfur, which radicals are optionally substituted by one or more groups which may be the same or different selected from halogen, ($C_1$-$C_6$)-alkoxy, ($C_1$-$C_6$)-haloalkoxy, ($C_1$-$C_2$)-alkylsulfynyl, ($C_1$-$C_2$)-alkylsulfonyl, ($C_3$-$C_6$)-cycloalkyl, ($C_1$-$C_4$)-alkoxycarbonyl, ($C_1$-$C_4$)-alkylcarbonyl and phenyl and in the case of cyclic radicals, also ($C_1$-$C_4$)-alkyl and ($C_1$-$C_4$)-haloalkyl;

$R^{36}$ is hydrogen; or $R^{36}$ is ($C_1$-$C_6$)-alkyl, ($C_2$-$C_6$)-alkenyl, ($C_2$-$C_6$)-alkynyl, which radicals are optionally substituted by one or more groups which may be the one or different selected from halogen, hydroxyl, ($C_1$-$C_4$)-alkyl, ($C_1$-$C_4$)-alkoxy and ($C_1$-$C_4$)-alkylthio;

$R^{37}$ is halogen, ($C_1$-$C_4$)-haloalkyl, ($C_1$-$C_4$)-haloalkoxy, nitro, ($C_1$-$C_4$)-alkyl, ($C_1$-$C_4$)-alkoxy, ($C_1$-$C_4$)-alkylsulfonyl, ($C_1$-$C_4$)-alkoxycarbonyl or ($C_1$-$C_4$)-alkylcarbonyl;

$R^{31}$ is hydrogen;

$R^{39}$ is halogen, nitro, ($C_1$-$C_4$)-alkyl, ($C_1$-$C_4$)-haloalkyl, ($C_1$-$C_4$)-haloalkoxy, ($C_3$-$C_6$)— cycloalkyl, phenyl, ($C_1$-$C_4$)-alkoxy, cyano, ($C_1$-$C_4$)-alkylthio, ($C_1$-$C_4$)-alkylsulfinyl, ($C_1$-$C_4$)-alkylsulfonyl, ($C_1$-$C_4$)-alkoxycarbonyl or ($C_1$-$C_4$)-alkylcarbonyl;

s is zero, 1 or 2, and o is 1 or 2.

The following sub-groups are particularly preferred amongst the antidotes of the formula (VI):

compounds in which $R^{48}$ and $R^{49}$ are H, ($C_1$-$C_8$)-alkyl, phenyl, phenyl-($C_1$-$C_8$)-alkyl, ($C_1$-$C_4$)-alkoxy-($C_1$-$C_8$)-alkyl, ($C_3$-$C_6$)-alkenyl or ($C_3$-$C_6$)-alkynyl, it being possible for phenyl rings to be substituted by F, Cl, Br, $NO_2$, CN, $OCH_3$, ($C_1$-$C_4$)-alkyl or $CH_3$—$SO_2$;

compounds in which $R^g$ is H;

compounds in which V is Y—$R^h$;

compounds in which E is oxygen;

compounds in which $Q^1$ is $CR_2^{47}$;

compounds in which $R^{47}$ is hydrogen;

compounds where m"=1 and E is oxygen or sulfur;

compounds in which m"=0;

compounds in which $R^{40}$, $R^{41}$, $R^{42}$, $R^{43}$ and $R^{44}$ are in each case hydrogen, E is oxygen, $Q^1$ is $CR_2^{47}$, V is Y—$R^h$ and m"=1, in particular those where $R^{47}$ is H, $R^b$ is $CH_3$ and Y is oxygen;

compounds in which $Q^1$ is $CR_2^{47}$ and m" is zero, in particular those in which $R^{44}$ and $R^{47}$ are hydrogen and V is Y—$R^h$, where $R^h$ is by preference methyl and Y is by preference oxygen.

The most especially preferred antidotes are flurazole, which is benzyl 2-chloro-4-trifluoromethyl-1,3-thiazole-5-carboxylate; fenchlorazole-ethyl, which is ethyl 1-(2,4-dichlorophenyl)-5-trichloromethyl-1H-1,2,4-triazole-3-carboxylate; fenchlorazole, which is 1-(2,4-dichlorophenyl)-5-trichloromethyl-1H-1,2,4-triazole-3-carboxylic acid; benoxacor, which is (±)-4-dichloroacetyl-3,4-dihydro-3-methyl-2H-1,4-benzoxazine; dichlormid, which is N,N-diallyl-2,2-dichloroacetamide; fenclorim, which is 4,6-dichloro-2-phenylpyrimidine; furilazole, which is (RS)-3-dichloroacetyl-5-(2-furyl)-2,2-dimethyloxazolidine; mefenpyr-diethyl, which is diethyl(RS)-1-(2,4-dichlorophenyl)-5-methyl-2-pyrazoline-3,5-dicarboxylate; CMPI, which is N-(4-chlorophenyl)maleimide; 4-hydroxy-1-methyl-3-(1-1H-tetrazol-5-ylmethanoyl)-1H-quinolin-2-one; daimuron, which is 1-(1-methyl-1-phenylethyl)-3-p-tolylurea; (S)-MBU, which is (S)-1-(1-alpha-methylbenzyl)-3-p-tolylurea; dimepiperate, which is S-1-methyl-1-phenylethyl piperidine-1-carbothioate; 5,5-diphenylisoxazoline-3-carboxylic acid; and ethyl 5,5-diphenylisoxazoline-3-carboxylate (most preferably fenchlorazole; CMPI; 4-hydroxy-1-methyl-3-(1-1H-tetrazol-5-ylmethanoyl)-1H-quinolin-2-one; (S)-MBU and dimepiperate).

The mixtures of the invention may be used to obtain selective weed control with low crop injury in various crop plants such as maize, soybean, cotton, canola, sugar beet, potatoes, wheat, tobacco, rice and oil seed rape. Preferred crops include maize, sugar beet, cotton and canola. Particularly preferred crop species are maize and soybean, especially maize.

Effective weed control coupled with low crop injury is a result of treatment of a plant locus with a combination of a herbicidal benzoylisoxazole and/or dione derivative and an antidote compound in accordance with the method of the present invention. By application to the 'plant locus' is meant application, for example to the plant growing medium, such as soil, as well as to the seeds, emerging seedlings, roots, stems, leaves or other plant parts.

The phrase 'combination of a herbicidal isoxazole and/or dione derivative and an antidote compound' includes various methods of treatment. For example, the soil of a plant locus may be treated with a "tank-mix" composition containing a mixture of the herbicide and the antidote which is "in combination", or the soil may be treated with the herbicide and antidote compounds separately so that the "combination" may be made on, or in the soil. After such treatments of the soil with a mixture of herbicide and antidote or by separate or sequential application of the herbicide and the antidote to the soil, the herbicide and antidote may be mixed into or incorporated into the soil either by mechanical mixing of the soil with implements or by "watering in" by rainfall or irrigation. The soil of a plant locus may also be treated with antidote by application of the antidote in a dispersible-concentrate form such as a granule. The granule may be applied to a furrow which is prepared for receipt of the crop seed and the herbicide may be applied to the plant locus either before or after in-furrow placement of the antidote-containing granule so that the herbicide and antidote form a "combination". Crop seed may be treated or coated with the antidote compound either while the crop seed is in-furrow just after seeding or, more commonly, the crop seed may be treated or coated with antidote prior to seeding into a furrow. The herbicide may be applied to the soil plant locus before or after seeding and a "combination" is made when both herbicide and an antidote-coated seed are in the soil.

In a preferred method of the invention (a) the herbicidal benzoylisoxazole and/or dione derivative and (b) antidote are applied separately such that the antidote contacts the seed or plant being treated before the herbicidal compound. Separate application can be achieved, for example, by dressing seed with antidote. The seed may also be treated, for example, at the time of planting, for example by applying antidote to seed in a seed furrow or to growing medium (for example soil) which then covers the seed. The herbicidal compound may then be applied to the surface of the growing medium (for example soil) or to a layer of soil above the layer containing antidote.

Apparatus suitable for planting seed, for example in a furrow and applying antidote to a layer of soil to cover the seed is generally known in the art. Herbicide may then be applied to the soil surface, for example by spraying a fluid formulation or distributing a solid formulation.

Separate application can also be achieved, for example, by applying the herbicidal compound and antidote simultaneously, preferably in a single composition, which composition permits contact of the antidote with the seed or plant before contact with the herbicidal compound.

For example the composition may comprise a delayed release formulation of the herbicidal compound, for example the antidote in the composition is released substantially immediately and before delayed release of the herbicidal compound. In one embodiment the method of the invention is preferably performed by applying the antidote directly to the seed before planting. This is generally effected by coating a quantity of crop seed with the antidote and thereafter planting the coated seed.

In a further preferred embodiment of the method of the invention, the antidotes are selected from fenchlorazole; CMPI; 4-hydroxy-1-methyl-3-(1-1H-tetrazol-5-ylmethanoyl)-1H-quinolin-2-one; (S)-MBU and dimepiperate.

The amount of a particular benzoylisoxazole and/or dione herbicide to be applied to the plant locus or crop-growing area will depend upon the nature of the weeds, the particular herbicide used, the time of application, the climate and the nature of the crop. Application rates of from about 0.004 kgha$^{-1}$ to 5 kgha$^{-1}$ herbicide are generally suitable, with a rate of about 0.01 kgha$^{-1}$ to 2 kgha$^{-1}$ being preferred, and with a rate of 0.005 kgha$^{-1}$ to 0.3 kgha$^{-1}$ being more preferred. The amount of antidote used in the method of the invention varies according to a number of parameters including the particular antidote employed, the crop to be protected, the amount and rate of herbicide applied, and the edaphic and climatic conditions prevailing. Also, the selection of the specific antidotes for use in the method of the invention, the manner in which it is to be applied and the determination of the activity which is non-phytotoxic but antidotally effective, can be readily performed in accordance with common practice in the art.

The antidote is applied in combination with the herbicide in a non-phytotoxic antidotally effective amount. By "non-phytotoxic" is meant an amount of the antidote which causes at most minor or no injury to the desired crop species. By "antidotally-effective" is meant an antidote used in an amount which is effective as an antidote with the herbicide to decrease the extent of injury caused by the herbicide to the desired crop species.

The herbicide/safener combination according to the invention may also be employed for controlling harmful plants in crops of genetically engineered plants which are either known or still to be developed. As a rule, the transgenic plants are distinguished by particular, advantageous properties, for example by resistances to certain crop protection agents, resistances to plant diseases or pathogens causing plant diseases such as particular insects or microorganisms such as fungi, bacteria or viruses. Other particular properties relate for example, to the harvested material in terms of quantity, quality, storing properties, composition and specific constituents. Thus, transgenic plants are known which have an increased starch content or an altered starch quality, or those where the harvested material has a different fatty acid composition.

The use of the combinations according to the invention in economically important transgenic crops of useful plants and ornamentals, for example cereals such as wheat, barley, rye, oats, panic grasses, rice, cassava and maize or else crops of sugar beet, cotton, soya, oilseed rape, potatoes, tomatoes, peas and other types of vegetables.

When the combinations according to the invention are applied in transgenic crops, effects on harmful plants to be observed in other crops are frequently accompanied by effects which are specific for application in the transgenic crop in question, for example an altered or specifically widened weed spectrum which can be controlled, altered application rates which may be used, preferably good compatibility with the herbicides to which the transgenic crop is resistant, and altered growth and yield of the transgenic crop plants.

The invention therefore also relates to the use of the combination according to the invention for controlling harmful plants in transgenic crop plants. The following non-limiting examples illustrate the invention wherein Antidote A is ethyl 5,5-diphenylisoxazoline-3-carboxylate and Antidote B is 5,5-diphenylisoxazoline-3-carboxylic acid.

Example 1

Maize seeds were sown in non-sterile loam and safener, dissolved in acetone was applied to the soil surface. After 30 minutes a treatment of herbicide, Compound A [5-cyclopropyl-4-(2-methylsulphonyl-4-trifluoromethylbenzoyl)isoxazole] was applied to the treated soil.

A visual assessment of the percentage phytotoxicity (measured as a reduction in green plant matter or plant height) compared to an untreated control was made 14 days after treatment (DAT).

Maize seeds were sown in non-sterile loam and grown up to a 1.5-2 leaf stage. Antidote, dissolved in acetone, was applied post-emergence to the soil surface. After 30 minutes a treatment of herbicide, Compound A [5-cyclopropyl-4-(2-methylsulphonyl-4-trifluoromethylbenzoyl)isoxazole] was applied to the treated soil.

A visual assessment of the percentage phytotoxicity compared with an untreated control was made 14 DAT.
Pre-Emergence Activity of Compound a on Maize in the Presence of Antidotes.

|   | g/ha of antidote | % phytotoxicity |
|---|---|---|
| Cpd A | 63 | 15 |
| Cpd A + mefenpyr-diethyl | 63 | 8.75 |
| Cpd A + fenchlorazole-ethyl | 63 | 11.3 |

-continued

|  | g/ha of antidote | % phytotoxicity |
|---|---|---|
| Cpd A + Antidote A | 63 | 11.3 |
| Cpd A + Antidote B | 63 | 8.75 |

Post-Emergence Activity of Compound A (63 g/ha) on Maize in the Presence of Antidotes.

|  | g/ha of antidote | % phytotoxicity |
|---|---|---|
| Cpd A | 63 | 27.5 |
| Cpd A + mefenpyr-diethyl | 63 | 25 |
| Cpd A + fenchlorazole-ethyl | 63 | 27.5 |
| Cpd A + Antidote A | 63 | 5 |
| Cpd A + Antidote B | 63 | 5 |

Post-Emergence Activity of Compound A (125 g/ha) on Maize in the Presence of Antidotes.

|  | g/h of antidote | % phytotoxicity |
|---|---|---|
| Cpd A | 125 | 43 |
| Cpd A + Antidote A | 31 | 15 |
| Cpd A + Antidote A | 63 | 10 |
| Cpd A + Antidote A | 125 | 15 |
| Cpd A + Antidote B | 31 | 19 |
| Cpd A + Antidote B | 63 | 18 |
| Cpd A + Antidote B | 125 | 25 |

According to a further feature of the present invention, there are provided herbicidal compositions comprising:
(a) a herbicidally effective amount of a benzoylisoxazole and/or dione derivative of formula (I) or an agriculturally acceptable salt or metal complex thereof; and
(b) an antidotally effective amount of an antidote compound or an agriculturally acceptable salt thereof;
in association with, and preferably homogeneously dispersed in, one or more compatible herbicidally-acceptable diluents or carriers and/or surface-active agents (i.e. diluents or carriers or surface-active agents of the type generally acceptable in the art as being suitable for use in herbicidal compositions and which are compatible with the herbicides of the present invention). In preferred compositions the antidote contacts the seed or plant being treated before the herbicidal compound. For example, the herbicidal compound may be in a delayed release composition. The term "homogeneously dispersed" is used to include compositions in which the benzoylisoxazole and/or dione of formula (I) and antidote are dissolved in the other components. The term "herbicidal composition" is used in a broad sense to include not only compositions which are ready for use as herbicides but also concentrates which must be diluted before use.

The ratio of herbicide to antidote may vary depending upon the crop to be protected, weed to be inhibited, herbicide used, etc., but normally an herbicide-to-antidote ratio ranging from 1:25 to 60:1 parts by weight may be employed, although much higher rates of antidote may be used, e.g., 1:100 to 1:300 parts by weight of herbicide to-antidote. The preferred weight ratio of herbicide-to-antidote is from 1:10 to 30:1. Another preferred weight range ratio is from 1:1 to 20:1, with an even more preferred weight ratio range from 2:1 to 15:1.

Preferably, the compositions contain from 0.05 to 90% by weight of benzoylisoxazole and/or dione of formula (I) and antidote.

The herbicidal composition may contain solid and liquid carriers and surface-active agents (e.g. wetters, dispersants or emulsifiers alone or in combination). Surface-active agents that may be present in the herbicidal compositions of the present invention may be of the ionic or non-ionic types, for example sulphoricinoleates, quaternary ammonium derivatives, products based on condensates of ethylene oxide with nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphono-succinates and alkali and alkaline earth metal salts of high molecular weight sulphonic acid derivatives such as sodium and calcium lignosulphonates. Examples of suitable solid diluents or carriers are aluminium silicate, talc, calcined magnesia, kieselguhr, tricalcium phosphate, powdered cork, absorbent carbon black and clays such as kaolin and bentonite. Examples of suitable liquid diluents include water, acetophenone, cyclohexanone, isophorone, toluene, xylene, and mineral, animal, and vegetable oils (these diluents may be used alone or in combination).

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Granular formulations may be prepared by absorbing the compounds of the present invention (dissolved in suitable solvents, which may, if desired, be volatile) onto the solid diluents or carriers in granular form and, if desired, evaporating the solvents, or by granulating compositions in powder form obtained as described above.

Powders, dispersible granules and liquid compositions in the form of concentrates may be diluted with water or other suitable diluents, for example mineral or vegetable oils, particularly in the case of liquid concentrates in which the diluent or carrier is an oil, to give compositions ready for use.

The wettable powders (or powders for spraying) usually contain from 20 to 95% of combination, and they usually contain, in addition to the solid vehicle, from 0 to 5% of a wetting agent, from 3 to 10% of a dispersant agent and if necessary, from 0 to 10% of one or more stabilisers and/or other additives such as penetrating agents, adhesives or anti-caking-agents and colourings.

The aqueous suspension concentrates, which are applicable by spraying, are prepared in such a way as to obtain a stable fluid product (by fine grinding) which does not settle out and they usually contain from 10 to 75% of combination, from 0.5 to 15% of surface acting agents, from 0.1 to 10% of thixotropic agents, from 0 to 10% of suitable additives such as antifoams, corrosion inhibitors, stabilisers, and water or an organic liquid in which the active substance is sparingly soluble or insoluble. Some organic solid substances or inorganic salts can be dissolved in order to assist in preventing sedimentation or as antifreeze for the water.

Application of the herbicide, antidote, or mixture thereof, can be carried out by conventional techniques utilizing, for example, hand-carried or tractor-mounted spreaders, power dusters, boom and hand sprayers, spray dusters, and granular applicators. If desired, application of the compositions of the invention to plants can be accomplished by incorporating the compositions in the soil or other media. Herbicidal compositions according to the present invention may also comprise (a) and (b) in association with, and preferably homogeneously dispersed in, one or more other pesticidally active compounds and, if desired one or more compatible pesticidally acceptable diluents and carriers. Examples of other pesticidally active ingredients include fungicides, insecticides, plant growth regulators and, most preferably, herbicides.

The optional partner herbicides which may be combined with the derivatives of formula (I) and antidote are preferably selected from chloroacetamides (e.g. metolachlor, acetochlor, alachlor), sulfonylureas, thiocarbamates, dithiocarbamates, metribuzin, sulfentrazone, flumetsulam, clorasulam-methyl, oxasulfuron, flumiclorac, bentazon, chlorimuron, linuron, clomazone, dimethenamid, pendimethalin, trifluralin, clethodim and acifluorfen, bifenox, diflufenican, diuron, atrazine and ametryne.

According to a further feature of the present invention there is provided a product comprising:
(a) a herbicidally effective amount of a benzoylisoxazole and/or dione derivative of formula (I), or an agriculturally acceptable salt or metal complex thereof; and
(b) an antidotally effective amount of an antidote compound or an agriculturally acceptable salt thereof;
as a combined preparation for separate, simultaneous or sequential use in the control of weeds at a crop locus, the antidote preferably contacting the seed or plant before the herbicidal compound.

The invention claimed is:
1. A method of reducing phytotoxicity to a crop at a locus caused by the application thereto of a herbicidal benzoylisoxazole and/or dione derivative of formula (I) or an agriculturally acceptable salt or metal complex thereof;
wherein the compound of formula (I) is a compound of the formula (Ia):

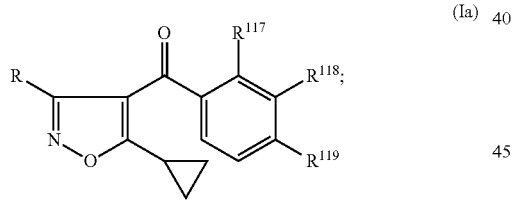

(Ia)

wherein:
R is selected from the group consisting of:
 a hydrogen atom;
 a halogen atom;
 a straight- or branched chain alkyl, alkenyl, or alkynyl group containing from one to six carbon atoms which is optionally substituted by one or more halogen atoms;
 —$CO_2R^3$; and
 —$CO^5$;
where:
 $R^3$ is a hydrogen atom, or a straight- or branched chain alkyl group containing up to six carbon atoms which is optionally substituted by one or more halogen atoms; and
 $R^5$ is a straight- or branched-chain alkyl group containing up to six carbon atoms which is optionally substituted by one or more halogen atoms, or a straight- or branched-chain alkenyl or alkynl group containing from two to six carbon atoms which is optionally substituted by one or more halogen atoms;
$R^{117}$ is selected from the group consisting of —$S(O)_p Me$ and —$CH_2 S(O)_q Me$;
$R^{118}$ is selected from the group consisting of a hydrogen atom, a chlorine atom, a bromine atom, and a fluorine atom;
$R^{119}$ is selected from the group consisting of a hydrogen atom, a chlorine atom, a bromine atom, a fluorine atom, and $CF_3$; and
p and q each independently have the values zero, one, or two;
which method comprises applying to the locus of the crop, before the herbicidal compound, an antidotally effective amount of an antidote compound, and optionally partner herbicide;
wherein the antidotally compound is a compound selected from the group consisting of ethyl 5,5-diphenylisoxazoline-3-carboxylate, and 5,5-diphenylisoxazoline-3-carboxylic acid; and
wherein the crop is maize.

2. A method of reducing phytotoxicity to a crop at a locus caused by the application thereto of a herbicidal benzoylisoxazole and/or dione derivative of formula (I) or an agriculturally acceptable salt or metal complex thereof, the formula (I) being represented by:

(I)

wherein:
A is a group (A-1):

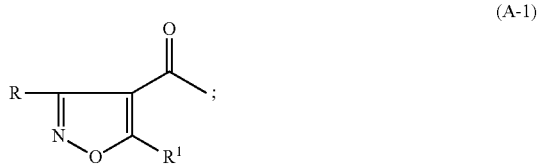

(A-1)

R is selected from the group consisting of:
 a hydrogen atom;
 a halogen atom;
 a straight- or branched chain alkyl, alkenyl, or alkynyl group containing from one to six carbon atoms which is optionally substituted by one or more halogen atoms;
 —$CO_2R^3$; and
 —$COR^5$; and
$R^1$ is:
 a straight- or branched-chain alkyl, alkenyl, or alkynyl group containing up to six carbon atoms which is optionally substituted by one or more halogen atoms; or
 a cycloalkyl group containing from three to six carbon atoms optionally substituted by one or more groups $R^5$ or one or more halogen atoms;

wherein:
R² is:
(A) selected from the group consisting of —S(O)$_p$R⁵, N(R⁸)SO₂R⁵, —OSO₂R⁵, —SO₂NR³R⁴, and —(CR⁹R¹⁰)$_y$—S(O)$_q$R⁵; or
(B) selected from the group consisting of a hydrogen atom, a chlorine atom, a bromine atom, and a fluorine atom; or
(C) selected from the group consisting of a hydrogen atom, a chlorine atom, a bromine atom, a fluorine atom, and CF₃;
wherein at least one R² is selected from the group (A); and
wherein:
z is three, and each R² is different;
R³ and R⁴ are each independently a hydrogen atom, or a straight-or branched-chain alkyl group containing up to six carbon atoms which is optionally substituted by one or more halogen atoms;
R⁵ is:
a straight- or branched-chain alkyl group containing up to six atoms which is optionally substituted by one or more halogen atoms; or
a straight- or branched-chain alkenyl or alkynyl group containing from two to six carbon atoms which is optionally substituted by one or more halogen atoms;
R⁸, R⁹, and R¹⁰ are each a hydrogen atom or R⁵;
p and q are each independently zero, one, or two; and
y is an integer from one to four, where when y is greater than one the groups R⁹ and R¹⁰ may be the same or different;
which method comprises applying to the locus of the crop, before the herbicidal compound, an antidotally effective amount of an antidote compound, and optionally partner herbicide;
wherein the antidote compound is a compound selected from the group consisting of ethyl 5,5-diphenylisoxazoline-3-carboxylate, and 5,5-diphenylisoxazoline-3-carboxylic acid; and
wherein the crop is maize.

3. The method as claimed in claim 2;
wherein:
R¹ is cyclopropyl.

4. The method according to claim 2;
in which the application rate of the benzoylisoxazole and/or dione of formula (I) is from 0.004 kg to 5 kg per hectare.

5. The method according to claim 2;
in which the application rate of the benzoylisoxazole and/or dione of formula (I) is from 0.01 kg to 2 kg per hectare.

6. A selective herbicidal composition comprising, in addition to customary inert formulation assistants:
a mixture of:
a) a herbicidally effective amount of a compound of formula I:

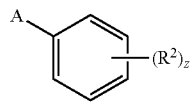

(I)

wherein:
A is a group (A-1):

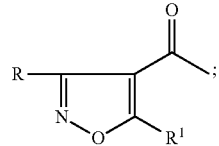

(A-1)

R is selected from the group consisting of:
a hydrogen atom;
a halogen atom;
a straight- or branched chain alkyl, alkenyl, or alkynyl group containing from one to six carbon atoms which is optionally substituted by one or more halogen atoms;
—CO₂R³; and
—COR⁵; and
R¹ is:
a straight- or branched-chain alkyl, alkenyl, or alkynyl group containing up to six carbon atoms which is optionally substituted by one or more halogen atoms; or
a cycloalkyl group containing from three to six carbon atoms optionally substituted by one or more groups R⁵ or one or more halogen atoms;
wherein:
R² is:
(A) selected from the group consisting of —S(O)$_p$,R⁵, N(R⁸)SO₂R⁵, —OSO₂R⁵, —SO₂NR³R⁴, and —(CR⁹R¹⁰)$_y$—S(O)$_q$R⁵; or
(B) selected from the group consisting of a hydrogen atom, a chlorine atom, a bromine atom, and a fluorine atom; or
(C) selected from the group consisting of a hydrogen atom, a chlorine atom, a bromine atom, a fluorine atom, and CF₃;
wherein at least one R² is selected from the group (A); and
wherein:
z is three, and each R² is different;
R³ and R⁴ are each independently a hydrogen atom, or a straight- or branched-chain alkyl group containing up to six carbon atoms which is optionally substituted by one or more halogen atoms;
R⁵ is:
a straight- or branched-chain alkyl group containing up to six atoms which is optionally substituted by one or more halogen atoms; or
a straight- or branched-chain alkenyl or alkynyl group containing from two to six carbon atoms which is optionally substituted by one or more halogen atoms;
R⁸, R⁹, and R¹⁰ are each a hydrogen atom or R⁵;
p and q are each independently zero, one, or two; and
y is an integer from one to four, where when y is greater than one the groups R⁹ and R¹⁰ may be the same or different; and
b) to antagonise the herbicide, an antidotally effective amount of an antidote compound selected from the group consisting of ethyl 5,5-diphenylisoxazoline-3-carboxylate, and 5,5-oliphenylisoxazoline-3-carboxylic acid;

wherein the amount of antidote compound is effective for reducing phytotoxicity to a crop.

7. A method of selectively controlling weeds and grasses in crops of cultivated plants, which comprises:
treating said cultivated plants, the seeds or seedlings, or the crop area thereof, concurrently or separately, with a herbicidally effective amount of the compound of formula I and, to antagonise the herbicide, an antidotally effective amount of the safener of formula II;
wherein herbicide and safener are as defined in claim 6; and
wherein the crop is maize.

8. A method of reducing phytotoxicity to a crop at a locus caused by the application thereto of a herbicidal benzoylisoxazole and/or dione derivative of formula (I) or an agriculturally acceptable salt or metal complex thereof, the formula (I) being represented by:

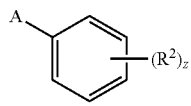
(I)

wherein:
A is a group (A-1):

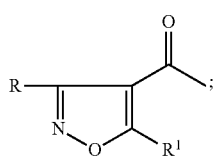
(A-1)

R is hydrogen;
R¹ is cyclopropyl;
(R²)_z is the combination of groups 4-CF₃ and 2-methylsulphonyl; and
z is two, and each R² is different;
which method comprises applying to the locus of the crop, before the herbicidal compound, an antidotally effective amount of an antidote compound, and optionally partner herbicide;
wherein the antidotally compound is a compound selected from the group consisting of ethyl 5,5-diphenylisoxazoline-3-carboxylate, and 5,5-diphenylisoxazoline-3-carboxylic acid; and
wherein the crop is maize.

9. The method as claimed in claim 8;
wherein the antidote compound is ethyl diphenylisoxazoline-3-carboxylate.

10. The method as claimed in claim 8;
wherein the antidote compound is diphenylisoxazoline-3-carboxylic acid.

11. A method of reducing phytotoxicity to a crop at a locus caused by the application thereto of a herbicidal compound, comprising:
applying to the locus of the crop, before the herbicidal compound, an antidotally effective amount of an antidote compound, and optionally partner herbicide;
wherein the herbicidal compound is isoxaflutole;
wherein the antidote compound is a compound selected from the group consisting of ethyl 5,5-diphenylisoxazoline-3-carboxylate, and 5,5-diphenylisoxazoline-3-carboxylic acid; and
wherein the crop is maize.

12. The method according to claim 11;
wherein the antidote compound is ethyl 5,5-diphenylisoxazoline-3-carboxylate.

13. The method according to claim 11;
wherein the antidote compound is 5,5-diphenylisozazoline-3-carboxylic acid.

14. The method according to one of claims 11-13;
wherein the application rate of the herbicidal compound is from 0.004 kg to 5 kg per hectare.

15. The method according to claim 14;
wherein the application rate of the herbicidal compound is from 0.01 kg to 2 kg per hectare.

16. The method according to one of claims 11-13;
wherein the weight ratio of the herbicidal compound to the antidote compound is 1:25 to 60:1.

17. The method according to claim 14;
wherein the weight ratio of the herbicidal compound to the antidote compound is 1:25 to 60:1.

18. The method according to claim 15;
wherein the weight ratio of the herbicidal compound to the antidote compound is 1:25 to 60:1.

19. A method of selectively controlling weeds and grasses in crops of cultivated plants, comprising:
treating said cultivated plants, the seeds or seedlings, or the crop area thereof, concurrently or separately, with:
a) a herbicidally effective amount of isoxaflutole; and
b) to antagonise the herbicide, an antidotally effective amount of an antidote compound selected from the group consisting of ethyl 5,5-diphenylisoxazoline-3-carboxylate, and 5,5-diphenylisoxazoline-3-carboxylic acid;
wherein the amount of antidote compound is effective for reducing phytotoxicity to the crop; and
wherein the crop is maize.

20. The method according to claim 19;
wherein the antidote compound is ethyl 5,5-diphenylisoxazoline-3-carboxylate.

21. The method according to claim 19;
wherein the antidote compound is 5,5-diphenylisoxazoline-3-carboxylic acid.

22. The method according to one of claims 19-21;
wherein the application rate of the isoxaflutole is from 0.004 kg to 5 kg per hectare.

23. The method according to claim 22;
wherein the application rate of the isoxaflutole is from 0.01 kg to 2 kg per hectare.

24. The method according to one of claims 19-21;
wherein the weight ratio of the isoxaflutole to the antidote compound is 1:25 to 60:1.

25. The method according to claim 22;
wherein the weight ratio of the isoxaflutole to the antidote compound is 1:25 to 60:1.

26. The method according to claim 23;
wherein the weight ratio of the isoxaflutole to the antidote compound is 1:25 to 60:1.

27. A selective herbicidal composition comprising, in addition to customary inert formulation assistants:
a mixture of:
a) a herbicidally effective amount of isoxaflutole; and
b) to antagonise the herbicide, an antidotally effective amount of an antidote compound selected from the group consisting of ethyl 5,5-diphenylisoxazoline-3-carboxylate, and 5,5-diphenylisoxazoline-3-carboxylic acid;
wherein the amount of antidote compound is effective for reducing phyto toxicity to a crop.

28. The selective herbicidal composition according to claim 27;
wherein the antidote compound is ethyl 5,5-diphenylisoxazoline-3-carboxylate.

29. The selective herbicidal composition according to claim 27;
wherein the antidote compound is 5,5-diphenylisoxazoline-3-carboxylic acid.

30. The selective herbicidal composition according to one of claims 27-29;
wherein the cultivate plants are maize.

31. The selective herbicidal composition according to one of claims 27-29;
wherein the weight ratio of the isoxaflutole to the antidote compound is 1:25 to 60:1.

32. The selective herbicidal composition according to claim 30;
wherein the weight ratio of the isoxaflutole to the antidote compound is 1:25 to 60:1.

33. A herbicidal composition comprising:
a mixture of
a) a herbicidally effective amount of isoxaflutole; and
b) to antagonise the herbicide, an antidotally effective amount of an antidote compound selected from the group consisting of ethyl 5,5-diphenylisoxazoline-3-carboxylate, and 5,5-diphenylisoxazoline-3-carboxylic acid;
wherein the amount of antidote compound is effective for reducing phytotoxicity to a crop.

34. The herbicidal composition according to claim 33;
wherein the antidote compound is ethyl 5,5-diphenylisoxazoline-3-carboxylate.

35. The selective herbicidal composition according to claim 33;
wherein the antidote compound is 5,5-diphenylisoxazoline-3-carboxylic acid.

36. The selective herbicidal composition according to one of claims 33-35;
wherein the cultivate plants are maize.

37. The selective herbicidal composition according to one of claims 33-35;
wherein the weight ratio of the isoxaflutole to the antidote compound is 1:25 to 60:1.

38. The selective herbicidal composition according to claim 36;
wherein the weight ratio of the isoxaflutole to the antidote compound is 1:25 to 60:1.

* * * * *